United States Patent

Okamura et al.

[11] Patent Number: 6,166,016
[45] Date of Patent: Dec. 26, 2000

[54] AMIDE DERIVATIVES

[75] Inventors: Takashi Okamura; Yasuo Shoji; Tadao Shibutani; Tsuneo Yasuda, all of Naruto; Takeshi Iwamoto, Komatsushima, all of Japan

[73] Assignee: Otsuka Pharmaceutical Factory, Inc., Tokushima, Japan

[21] Appl. No.: 09/194,727

[22] PCT Filed: Jun. 2, 1997

[86] PCT No.: PCT/JP97/01875

§ 371 Date: Dec. 2, 1998

§ 102(e) Date: Dec. 2, 1998

[87] PCT Pub. No.: WO97/46560

PCT Pub. Date: Nov. 12, 1997

[30] Foreign Application Priority Data

Jun. 6, 1996 [JP] Japan ................................. 8-144099
Mar. 26, 1997 [JP] Japan ................................. 9-073116

[51] Int. Cl.[7] ..................... C07C 233/64; C07D 473/34; C07D 487/04; A61K 31/166; A61K 31/52
[52] U.S. Cl. ..................... 514/246; 514/258; 514/261; 514/245; 544/211; 544/262; 544/277; 544/278
[58] Field of Search ..................... 544/211, 262, 544/277, 278; 514/245, 246, 258, 261

[56] References Cited

U.S. PATENT DOCUMENTS

| 3,682,918 | 8/1972 | Druey et al. ................. 260/256.4 F |
| 4,638,010 | 1/1987 | Weller, III et al. ................. 514/423 |
| 5,391,739 | 2/1995 | Peet et al. ................. 544/277 |
| 5,688,949 | 11/1997 | Inoue et al. ................. 544/281 |
| 5,869,486 | 2/1999 | Lee et al. ................. 514/248 |

FOREIGN PATENT DOCUMENTS

WO 94/13676  6/1994  WIPO.
WO 94/13677  6/1994  WIPO.
WO 95/33750  12/1995  WIPO.

*Primary Examiner*—Mukund J. Shah
*Assistant Examiner*—Deepak R. Rao
*Attorney, Agent, or Firm*—Sughrue, Mion, Zinn, Macpeak & Seas, PLLC

[57] ABSTRACT

The invention provides amide derivatives which are useful as analgesics, anti-inflammatory agents, antimicrobial drugs, hypoglycemic agents, hypolipidemic agents, antihypertensive agents, anti-cancer agents, etc., the derivatives being represented by the formula

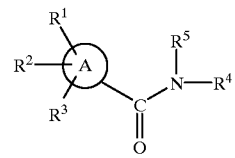

wherein ring A represents a benzene ring, a naphthalene ring, a pyridine ring or a furan ring; $R^4$ represents a heterocyclic group selected from the group consisting of a lower alkyl-substituted thieno[3,2-d]pyrimidin-4-yl group, an optionally substituted pyrazolo[1,5-a]-1,3,5-triazin-4-yl group, a pyrazolo[3,4-d]pyrimidin-4-yl group substituted at the 6-position and a purin-6-yl group substituted at the 2-position; and $R^5$ represents a hydrogen atom or a group represented by

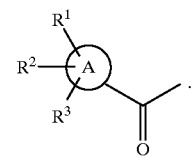

7 Claims, No Drawings

AMIDE DERIVATIVES

This application is a 371 of PCT/JP97/01875 filed Jun. 2, 1997.

TECHNICAL FIELD

The present invention relates to novel amide derivatives.

PRIOR ART

The derivatives of the invention are novel compounds which have not been published in any literature. An object of this invention is to provide compounds useful as medicine.

DISCLOSURE OF THE INVENTION

The present invention provides novel derivatives represented by the following formula (1).

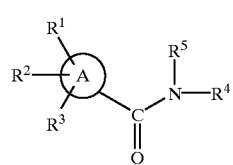

(1)

In the formula (1), ring A represents a benzene ring, a naphthalene ring, a pyridine ring or a furan ring; when ring A is other than a benzene ring, $R^1$, $R^2$ and $R^3$ are all hydrogen atoms, and when ring A is a benzene ring, $R^1$, $R^2$ and $R^3$ are the same or different and independently represent hydrogen, lower alkoxy, halogen, nitro, lower alkyl, halogen-substituted lower alkyl, phenyl, phenoxy, lower alkanoyloxy, hydroxy, lower alkylthio, lower alkylsulfinyl or lower alkylsulfonyl.

Further, $R^4$ represents a heterocyclic group selected from the group consisting of:
(1) a lower alkyl-substituted thieno[3,2-d]pyrimidin-4-yl group;
(2) a pyrazolo[1,5-a]-1,3,5-triazin-4-yl group optionally having one or two substituents selected from the group consisting of lower alkyl, phenyl, phenyl(lower)alkyl, phenylthiophenyl and halogen;
(3) a pyrazolo[3,4-d]pyrimidin-4-yl group which has a lower alkyl group at the 6-position and one of whose nitrogen atoms may have a phenyl(lower)alkyl group as a substituent; and
(4) a purin-6-yl group which has a lower alkyl group at the 2-position and one of whose nitrogen atoms may have a lower alkyl or phenyl(lower)alkyl group as a substituent.

Further, $R^5$ represents a hydrogen atom or a group represented by

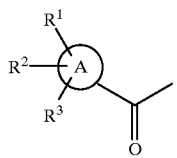

wherein A, $R^1$, $R^2$ and $R^3$ are as defined above.

Examples of the groups in the formula (1) are shown below. As regards the groups, the term "lower" means $C_{1-6}$.

The lower alkyl group includes straight- or branched-chain lower alkyl groups such as methyl, ethyl, propyl, isopropyl, butyl, isobutyl, tert-butyl, pentyl, hexyl and the like.

The lower alkoxy group includes methoxy, ethoxy, propoxy, isopropoxy, butoxy, pentyloxy, hexyloxy and the like.

The phenyl(lower)alkyl group includes benzyl, 1-phenylethyl, 2-phenylethyl, 3-phenylpropyl, 4-phenylbutyl, 5-phenylpentyl, 6-phenylhexyl and the like.

The halogen atom includes fluorine, chlorine, bromine and iodine.

The halogen-substituted lower alkyl group includes trifluoromethyl, pentafluoroethyl, heptafluoropropyl, nonafluorobutyl, undecafluoropentyl, tridecafluorohexyl and the like.

The (lower)alkanoyloxy group includes acetoxy, propionyloxy, butyryloxy, valeryloxy, hexanoyloxy, heptanoyloxy and the like.

The lower alkylthio group includes methylthio, ethylthio, propylthio, butylthio, pentylthio, hexylthio and the like.

The lower alkylsulfinyl group includes methylsulfinyl, ethylsulfinyl, propylsulfinyl, butylsulfinyl, pentylsulfinyl, hexylsulfinyl and the like.

The lower alkylsulfonyl group includes methylsulfonyl, ethylsulfonyl, propylsulfonyl, butylsulfonyl, pentylsulfonyl, hexylsulfonyl and the like.

Of the heterocyclic groups represented by $R^4$, examples of (1) lower alkyl-substituted thieno[3,2-d]pyrimidin-4-yl groups are 2-methylthieno[3,2-d]pyrimidin-4-yl, 2-ethylthieno[3,2-d]pyrimidin-4-yl, 2-n-propylthieno[3,2-d]pyrimidin-4-yl, 2-n-butylthieno[3,2-d]pyrimidin-4-yl, 2-n-pentylthieno[3,2-d]pyrimidin-4-yl, 2-n-hexylthieno[3,2-d]pyrimidin-4-yl and the like.

Of the heterocyclic groups represented by $R^4$, examples of (2) pyrazolo[1,5-a]-1,3,5-triazin-4-yl groups optionally having one or two substituents selected from the group consisting of lower alkyl, phenyl, phenyl(lower)alkyl, phenylthiophenyl and halogen include unsubstituted pyrazolo[1,5-a]-1,3,5-triazin-4-yl and the following substituted groups:
2-methylpyrazolo[1,5-a]-1,3,5-triazin-4-yl, 2-ethylpyrazolo[1,5-a]-1,3,5-triazin-4-yl, 2-n-propylpyrazolo[1,5-a]-1,3,5-triazin-4-yl, 2-n-butylpyrazolo[1,5-a]-1,3,5-triazin-4-yl, 2-n-pentylpyrazolo[1,5-a]-1,3,5-triazin-4-yl, 2-n-hexylpyrazolo[1,5-a]-1,3,5-triazin-4-yl, 2-phenylpyrazolo[1,5-a]-1,3,5-triazin-4-yl, 2-benzylpyrazolo[1,5-a]-1,3,5-triazin-4-yl, 2-(2-phenylethyl)pyrazolo[1,5-a]-1,3,5-triazin-4-yl, 2-(3-phenylpropyl)pyrazolo[1,5-a]-1,3,5-triazin-4-yl, 2-(4-phenylbutyl)pyrazolo[1,5-a]-1,3,5-triazin-4-yl, 2-(5-phenylpentyl)pyrazolo[1,5-a]-1,3,5-triazin-4-yl, 2-(6-phenylhexyl)pyrazolo[1,5-a]-1,3,5-triazin-4-yl, 2-methyl-8-phenylpyrazolo[1,5-a]-1,3,5-triazin-4-yl, 2-ethyl-8-phenylpyrazolo[1,5-a]-1,3,5-triazin-4-yl, 8-phenyl-2-n-propylpyrazolo[1,5-a]-1,3,5-triazin-4-yl, 2-n-butyl-8-phenylpyrazolo[1,5-a]-1,3,5-triazin-4-yl, 2-n-pentyl-8-phenylpyrazolo[1,5-a]-1,3,5-triazin-4-yl, 2-n-hexyl-8-phenylpyrazolo[1,5-a]-1,3,5-triazin-4-yl, 2-methyl-7-phenylpyrazolo[1,5-a]-1,3,5-triazin-4-yl, 2-ethyl-7-phenylpyrazolo[1,5-a]-1,3,5-triazin-4-yl, 7-phenyl-2-n-propylpyrazolo[1,5-a]-1,3,5-triazin-4-yl, 2-n-butyl-7-phenylpyrazolo[1,5-a]-1,3,5-triazin-4-yl, 2-n-pentyl-7-phenylpyrazolo[1,5-a]-1,3,5-triazin-4-yl, 2-n-hexyl-7-phenylpyrazolo[1,5-a]-1,3,5-triazin-4-yl, 2-methyl-8-(4-phenylthiophenyl)pyrazolo[1,5-a]-1,3,5-triazin-4-yl, 2-ethyl-8-(4-phenylthiophenyl)pyrazolo[1,5-a]-1,3,5-triazin-4-yl, 8-(4-phenylthiophenyl)-2-n-propylpyrazolo[1,5-a]-1,3,5-triazin-4-yl, 2-n-butyl-8-(4-phenylthiophenyl)pyrazolo[1,5-a]-1,3,5-triazin-4-yl, 2-n-pentyl-8-(4-phenylthiophenyl)pyrazolo[1,5-a]-1,3,5-triazin-4-yl, 2-n-hexyl-8-(4-phenylthiophenyl)pyrazolo[1,5-a]-1,3,5-triazin- 4-yl, 8-bromo-2-methylpyrazolo[1,5-a]-1,3,5-triazin-4-yl, 8-bromo-2-ethylpyrazolo[1,5-a]-1,3,5-triazin-4-yl, 8-bromo-2-n-propylpyrazolo[1,5-a]-1,3,5-triazin-4-yl, 8-bromo-2-n-butylpyrazolo[1,5-a]-1,3,5-triazin-4-yl, 8-bromo-2-n-pentylpyrazolo[1,5-a]-1,3,5-triazin-4-yl, 8-bromo-2-n-hexylpyrazolo[1,5-a]-1,3,5-triazin-4-yl, 2-n-butyl-8-fluoropyrazolo[1,5-a]-1,3,5-triazin-4-yl, 2-n-butyl-8-chloropyrazolo[1,5-a]-1,3,5-triazin-4-yl, 2-n-butyl-8-iodopyrazolo[1,5-a]-1,3,5-triazin-4-yl and the like.

Of the heterocyclic groups represented by $R^4$, given below are examples of (3) pyrazolo[3,4-d]pyrimidin-4-yl groups which have a lower alkyl group at the 6-position and one of whose nitrogen atoms may have a phenyl(lower)alkyl group as a substituent. 6-Methyl-1H-pyrazolo[3,4-d]pyrimidin-4-yl, 6-ethyl-1H-pyrazolo[3,4-pyrimidin-4-yl, 6-n-propyl-1H-pyrazolo[3,4-d]pyrimidin-4-yl, 6-n-butyl-1H-pyrazolo[3,4-d]pyrimidin-4-yl, 6-n-pentyl-1H-pyrazolo[3,4-d]pyrimidin-4-yl, 6-n-hexyl-1H-pyrazolo[3,4-d]pyrimidin-4-yl, 6-methyl-2H-pyrazolo[3,4-d]pyrimidin-4-yl, 6-ethyl-2H-pyrazolo[3,4-d]pyrimidin-4-yl, 6-n-propyl-2H-pyrazolo[3,4-d]pyrimidin-4-yl, 6-n-butyl-2H-pyrazolo[3,4-d]pyrimidin-4-yl, 6-n-pentyl-2H-pyrazolo[3,4-d]pyrimidin-4-yl, 6-n-hexyl-2H-pyrazolo[3,4-d]pyrimidin-4-yl, 2-benzyl-6-methyl-2H-pyrazolo[3,4-d]pyrimidin-4-yl, 2-benzyl-6-ethyl-2H-pyrazolo[3,4-d]pyrimidin-4-yl, 2-benzyl-6-n-propyl-2H-pyrazolo[3,4-d]pyrimidin-4-yl, 2-benzyl-6-n-butyl-2H-pyrazolo[3,4-d]pyrimidin-4-yl, 2-benzyl-6-n-pentyl-2H-pyrazolo[3,4-d]pyrimidin-4-yl, 2-benzyl-6-n-hexyl-2H-pyrazolo[3,4-d]pyrimidin-4-yl, 6-n-butyl-2-(1-phenylethyl)-2H-pyrazolo[3,4-d]pyrimidin-4-yl, 6-n-butyl-2-(2-phenylethyl)-2H-pyrazolo[3,4-d]pyrimidin-4-yl, 6-n-butyl-2-(3-phenylpropyl)-2H-pyrazolo[3,4-d]pyrimidin-4-yl, 6-n-butyl-2-(4-phenylbutyl)-2H-pyrazolo[3,4-d]pyrimidin-4-yl, 6-n-butyl-2-(5-phenylpentyl)-2H-pyrazolo[3,4-d]pyrimidin-4-yl, 6-n-butyl-2-(6-phenylhexyl)-2H-pyrazolo[3,4-d]pyrimidin-4-yl, 1-benzyl-6-methyl-1H-pyrazolo[3,4-d]pyrimidin-4-yl, 1-benzyl-6-ethyl-1H-pyrazolo(3,4-d]pyrimidin-4-yl, 1-benzyl-6-n-propyl-1H-pyrazolo[3,4-d]pyrimidin-4-yl, 1-benzyl-6-n-butyl-1H-pyrazolo[3,4-d]pyrimidin-4-yl, 1-benzyl-6-n-pentyl-1H-pyrazolo[3,4-d]pyrimidin-4-yl, 1-benzyl-6-n-hexyl-1H-pyrazolo[3,4-d]pyrimidin-4-yl, 6-n-butyl-1-(1-phenylethyl)-1H-pyrazolo[3,4-d]pyrimidin-4-yl, 6-n-butyl-1-(2-phenylethyl)-1H-pyrazolo[3,4-d]pyrimidin-4-yl, 6-n-butyl-1-(3-phenylpropyl)-1H-pyrazolo[3,4 -d]pyrimidin-4-yl, 6-n-butyl-1-(4-phenylbutyl)-1H-pyrazolo[3,4-d]pyrimidin-4-yl, 6-n-butyl-1-(5-phenylpentyl)-1H-pyrazolo[3,4-d]pyrimidin-4-yl, 6-n-butyl-1-(6-phenylhexyl)-1H-pyrazolo[3,4-d]pyrimidin-4-yl, 6-n-butyl-5H-pyrazolo[3,4-d]pyrimidin-4-yl, 5-benzyl-6-n-butyl-5H-pyrazolo[3,4-d]pyrimidin-4-yl and the like.

Of the heterocyclic groups represented by $R^4$, given below are examples of (4) purin-6-yl groups which have a lower alkyl group at the 2-position and one of whose nitrogen atoms may have a lower alkyl or phenyl(lower) alkyl group as a substituent. 2-Methyl-9H-purin-6-yl, 2-ethyl-9H-purin-6-yl, 2-n-propyl-9H-purin-6-yl, 2-n-butyl-9H-purin-6-yl, 2-n-pentyl-9H-purin-6-yl, 2-n-hexyl-9H-purin-6-yl, 2-methyl-7H-purin-6-yl, 2-ethyl-7H-purin-6-yl, 2-n-propyl-7-H-purin-6-yl, 2-n-butyl-7H-purin-6-yl, 2-n-pentyl-7H-purin-6-yl, 2-n-hexyl-7H-purin-6-yl, 9-methyl-9H-purin-6-yl, 9-benzyl-2-ethyl-9H-purin-6-yl, 9-benzyl-2-n-propyl-9H-purin-6-yl, 9-benzyl-2-n-butyl-9H-purin-6-yl, 9-benzyl-2-n-pentyl-9H-purin-6-yl, 9-benzyl-2-n-hexyl-9H-purin-6-yl, 2-n-butyl-9-(1-phenylethyl)-9H-purin-6-yl, 2-n-butyl-9-(2-phenylethyl)-9H-purin-6-yl, 2-n-butyl-9-(3-phenylpropyl)-9H-purin-6-yl, 2-n-butyl-9-(4-phenylbutyl)-9H-purin-6-yl, 2-n-butyl-9-(5-phenylpentyl)-9H-purin-6-yl, 2-n-butyl-9-(6-phenylhexyl)-9H-purin-6-yl, 2,9 -dimethyl-9H-purin-6-yl, 2-ethyl-9-methyl-9H-purin-6-yl, 9-methyl-2-n-propyl-9H-purin-6-yl, 2-n-butyl-9-methyl-9H-purin-6-yl, 9-methyl-2-n-pentyl-9H-purin-6-yl, 2-n-hexyl-9-methyl-9H-purin-6-yl, 7-benzyl-2-methyl-7H-purin-6-yl, 7-benzyl-2-ethyl-7H-purin-6-yl, 7-benzyl-2-n-propyl-7H-purin-6-yl, 7-benzyl-2-n-butyl-7H-purin-6-yl, 7-benzyl-2-n-pentyl-7H-purin-6-yl, 7-benzyl-2-n-hexyl-7H-purin-6-yl, 2-n-butyl-7-(1-phenylethyl)-7H-purin-6-yl, 2-n-butyl-7-(2-phenylethyl)-7H-purin-6-yl, 2-n-butyl-7-(3-phenylpropyl)-7H-purin-6-yl, 2-n-butyl-7-(4-phenylbutyl)-7H-purin-6-yl, 2-n-butyl-7-(5-phenylpentyl)-7H-purin-6-yl, 2-n-butyl-7-(6-phenylhexyl)-7H-purin-6-yl, 2,7-dimethyl-7H-purin-6-yl, 2-ethyl-7-methyl-7H-purin-6-yl, 7-methyl-2-n-propyl-7H-purin-6-yl, 2-n-butyl-7-methyl-7H-purin-6-yl, 7-methyl-2-n-pentyl-7H-purin-6-yl, 2-n-hexyl-7-methyl-7H-purin-6-yl, 1-benzyl-2-methyl-1H-purin-6-yl, 1-benzyl-2-ethyl-1H-purin-6-yl, 1-benzyl-2-n-propyl-1H-purin-6-yl, 1-benzyl-2-n-butyl-1H-purin-6-yl, 1-benzyl-2-n-pentyl-1H-purin-6-yl, 1-benzyl-2-n-hexyl-1H-purin-6-yl, 2-n-butyl-1-(1-phenylethyl)-1H-purin-6-yl, 2-n-butyl-1-(2-phenylethyl)-1H-purin-6-yl, 2-n-butyl-1-(3-phenylpropyl)-1H-purin-6-yl, 2-n-butyl-1-(4-phenylbutyl)-1H-purin-6-yl, 2-n-butyl-1-(5-phenylpentyl)-1H-purin-6-yl, 2-n-butyl-1-(6-phenylhexyl)-1H-purin-6-yl, 1,2-dimethyl-1H-purin-6-yl, 2-ethyl-1-methyl-1H-purin-6-yl, 1-methyl-2-n-propyl-1H-purin-6-yl, 2-n-butyl-1-methyl-1H-purin-6-yl, 1-methyl-2-n-pentyl-1H-purin-6-yl, 2-n-hexyl-1-methyl-1H-purin-6-yl and the like.

The amide derivatives of the invention are useful as medicine, and particularly useful as analgesics (for relieving postoperative pain, migraine, gout, chronic pain, neuropathic pain, cancer pain, etc.), anti-inflammatory agents, antimicrobial drugs, hypoglycemic agents, hypolipidemic agents, antihypertensive agents, anti-cancer agents, etc. The derivatives of the invention are highly suitable for use as analgesics which are characterized by being free of side effects typically seen in conventional analgesics.

Examples of the derivatives of the invention suitable for the above medicinal use are those of formula (1) wherein A is a benzene ring, and particularly those wherein A is a benzene ring and the heterocyclic group $R^4$ is either a thieno[3,2-d]pyrimidin-4-yl group substituted by a lower alkyl group at the 2-position or a pyrazolo[1,5-a]-1,3,5-triazin-4-yl group substituted by a lower alkyl group at the 2-position. Among the suitable derivatives, more preferable are those wherein $R^1$, $R^2$ and $R^3$ are the same or different and independently represent hydrogen, lower alkoxy, halogen, phenyl, lower alkanoyloxy or lower alkylthio.

Examples of particularly preferable amide derivatives of the invention are shown below.

N-(2-n-butylpyrazolo[1,5-a]-1,3,5-triazin-4-yl)-3,4,5-trimethoxybenzamide;

N-(2-n-butylpyrazolo[1,5-a]-1,3,5-triazin-4-yl)-2,4-dichlorobenzamide;

N-(2-n-butylpyrazolo[1,5-a]-1,3,5-triazin-4-yl)-3-chlorobenzamide; and

N-(2-n-butylthieno[3,2-d]pyrimidin-4-yl)-3,4,5-trimethoxybenzamide.

The derivatives of the invention can be produced by various processes. Exemplary processes are schematically shown below.

[Reaction Scheme-1]

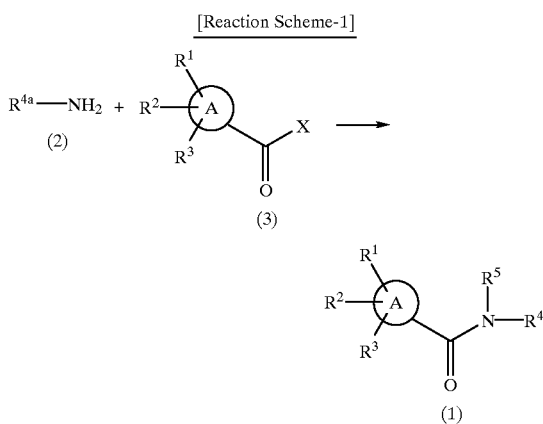

wherein A, $R^1$, $R^2$, $R^3$, $R^4$ and $R^5$ are as defined above, X is a halogen atom, and $R^{4a}$ is a heterocyclic group selected from the following groups (1), (2), (3') and (4'):
(1) a lower alkyl-substituted thieno[3,2-d]pyrimidin-4-yl group;
(2) a pyrazolo[1,5-a]-1,3,5-triazin-4-yl group optionally having one or two substituents selected from the group consisting of lower alkyl, phenyl, phenyl(lower)alkyl, phenylthiophenyl and halogen;
(3') a pyrazolo[3,4-d]pyrimidin-4-yl group which has a lower alkyl group at the 6-position and one of whose nitrogen atoms may have a phenyl(lower)alkyl or a suitable protective group as a substituent; and
(4') a purin-6-yl group which has a lower alkyl group at the 2-position and one of whose nitrogen atoms may have a lower alkyl, phenyl(lower)alkyl or a suitable protective group as a substituent.

As shown in the above Reaction Scheme-1, the compound (2) and acid halide (3) are reacted to produce a compound (1) of the invention. The reaction can be carried out in a suitable solvent in the presence of a deacidification agent. Examples of useful solvents are aromatic or aliphatic hydrocarbons such as benzene, toluene, xylene and petroleum ether; chain or cyclic ethers such as diethyl ether, dimethoxyethane, tetrahydrofuran (THF) and 1,4-dioxane; ketones such as acetone, ethyl methyl ketone and acetophenone; and halogenated hydrocarbons such as dichloromethane, chloroform, carbon tetrachloride and 1,2-dichloroethane. Examples of preferable deacidification agents are tertiary amines such as triethylamine, N,N-diethylaniline, N-methylmorpholine, pyridine and 4-dimethylaminopyridine.

In the above reaction, there is no limitation on the amounts of acid halide (3) and deacidification agent relative to the compound (2). However, they are preferably used in an approximately equimolar to excessive molar amount respectively. The reaction is carried out at 0° C. to reflux temperature and completed in about 0.5–200 hours.

When acid halide (3) is used in an approximately equimolar amount, a compound (1) wherein $R^5$ is hydrogen is produced as a main product. By increasing the amount of acid halide or extending the reaction time, an increased amount of the compound (1) wherein $R^5$ is other than hydrogen can be produced.

As regards suitable protective groups of the heterocyclic group $R^{4a}$ defined in (3') and (4') in Reaction Scheme-1, examples are usual protective groups automatically deprotected by the above reaction, such as benzyloxycarbonyl, t-butoxycarbonyl, fluorenylmethyloxycarbonyl, 2,2,2-trichloroethoxycarbonyl and the like. These protective groups are usually deprotected automatically by the above reaction, and even if some remain protected, the groups can be easily deprotected, for example, by hydrolysis in a solvent such as methanol or ethanol in the presence of a catalyst such as palladium-carbon at room temperature for about 1–30 hours, or reductive deprotection with zinc powder in water or acetic acid, or treatment with a strong acid such as hydrochloric acid or trifluoroacetic acid.

The starting compound (2) can be prepared, for example, by the following method shown in Reaction Scheme-2 to Reaction Scheme-6.

[Reaction Scheme-2]

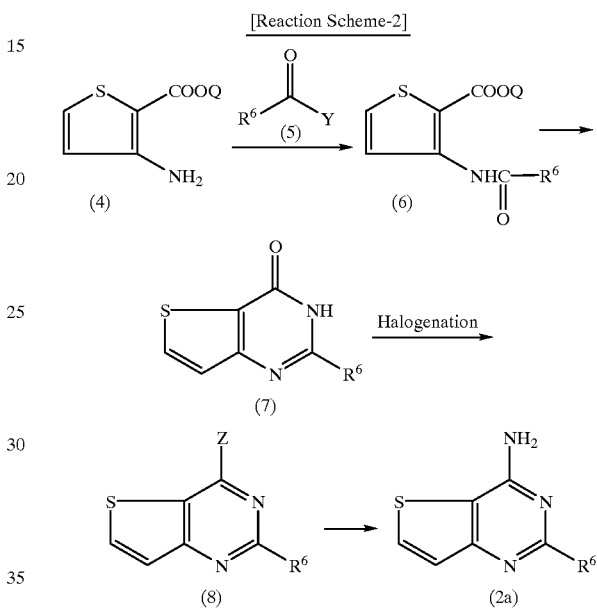

wherein $R^6$ are lower alkyl, Q is lower alkyl, and Y and Z are each halogen.

In Reaction Scheme-2, 3-aminothiophene-2-carboxylate (4) is reacted with an equimolar to slightly excessive molar amount of acid halide (5) in an amine solvent such as pyridine, lutidine or triethylamine at about 0° C. to room temperature for about 1–10 hours to produce an amide (6).

The amide (6) is subjected to cyclic reaction in ammonia water at about 80° C. to reflux temperature for about 10 to 50 hours to produce a compound (7).

The subsequent halogenation of the compound (7) obtained by the above reaction is carried out in the presence of a deacidification agent such as N,N-dimethylaniline, N,N-diethylaniline or triethylamine using a halogenating agent such as phosphorus oxychloride or phosphorus oxybromide. Since the above-mentioned halogenating agents also function as solvents, there is no need to use any solvents in the above reaction. The reaction can also proceed using inert solvents such as benzene, toluene, xylene or the like. In the above reaction, the amount of the deacidification agent is preferably about 1–10 times the molar amount of the compound (7). The reaction is carried out at room temperature to the reflux temperature of the solvent and completed in about 5–50 hours.

The compound (8) thus obtained can be converted into a compound (2a) by treatment with ammonia water. This reaction is carried out by heating the compound (8) in ammonia water at about 70° C. to reflux temperature for about 5 to 30 hours.

[Reaction Scheme-3]

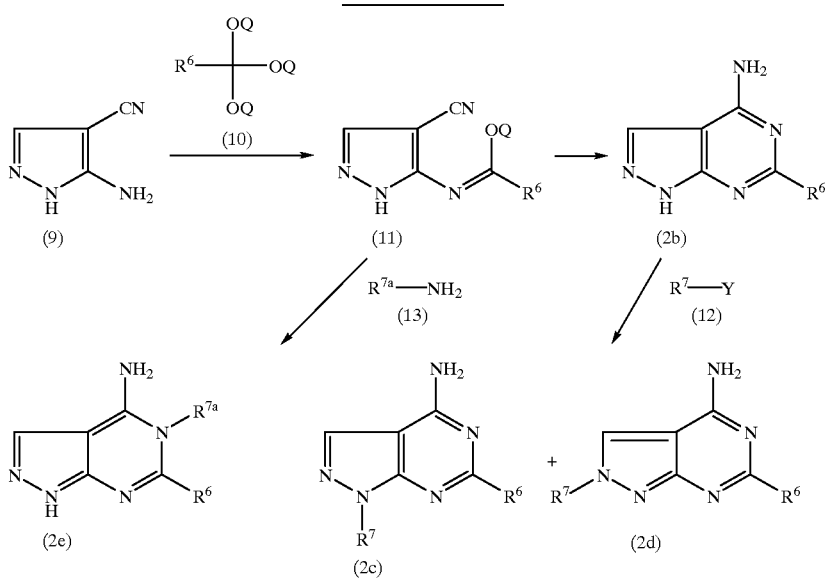

wherein $R^6$, Q and Y are as defined above, $R^7$ is phenyl (lower)alkyl or a suitable protective group and $R^{7a}$ is phenyl(lower)alkyl.

In Reaction Scheme-3, the pyrazole derivative (9) is reacted with an equimolar to excessive molar amount of ortho-acid-ester (10) in an inert solvent such as N,N-dimethylformamide (DMF), N,N-dimethylacetamide (DMA) or dimethyl sulfoxide (DMSO) at approximately reflux temperature for 10 minutes to 1 hour to produce a compound (11).

Subsequently the compound (11) can be converted into a compound (2b) by reaction with an excessive amount of ammonia in an inert solvent such as methanol, ethanol or ethylene glycol. The reaction is carried out at about 0° C. to room temperature and completed in about 10 to 50 hours.

The compound (2b) can be converted into compounds (2c) and (2d) by reaction with halide (12). The reaction is carried out in an inert solvent such as DMF, DMA or DMSO in the presence of a base such as sodium hydride, potassium hydride, sodium ethoxide, sodium carbonate or triethylamine. In the reaction, halide (12) and a base are used preferably in an approximately equimolar to excessive molar amount relative to the starting compound. The reaction is usually carried out with ice-cooling and completed in about 0.5–10 hours.

Also, the compound (11) can be converted into a compound (2e) by reaction with an amine (13) in an inert solvent such as methanol, ethanol or ethylene glycol. Using the amine (13) in an amount of 1 to 2 equivalents, the reaction is carried out at about room temperature to reflux temperature for about 1–10 hours, thus providing a compound (2e).

[Reaction Scheme-4]

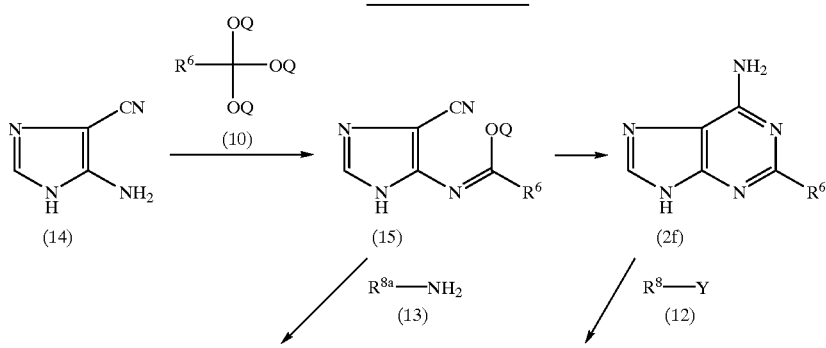

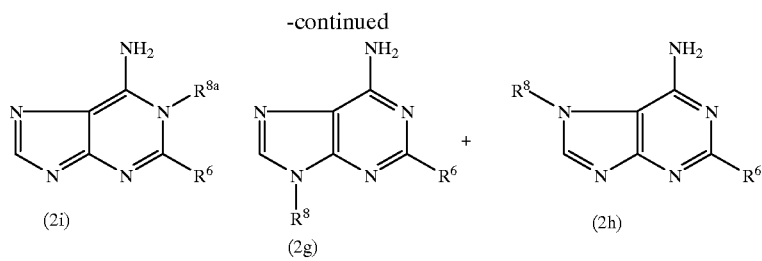

wherein $R^6$, Q and Y are as defined above, $R^8$ is lower alkyl, phenyl(lower)alkyl or a suitable protective group and $R^{8a}$ is lower alkyl or phenyl(lower)alkyl.

The reactions shown in Reaction Scheme-4 can be carried out in a similar manner as the corresponding reactions in Reaction Scheme-3.

[Reaction Scheme-5]

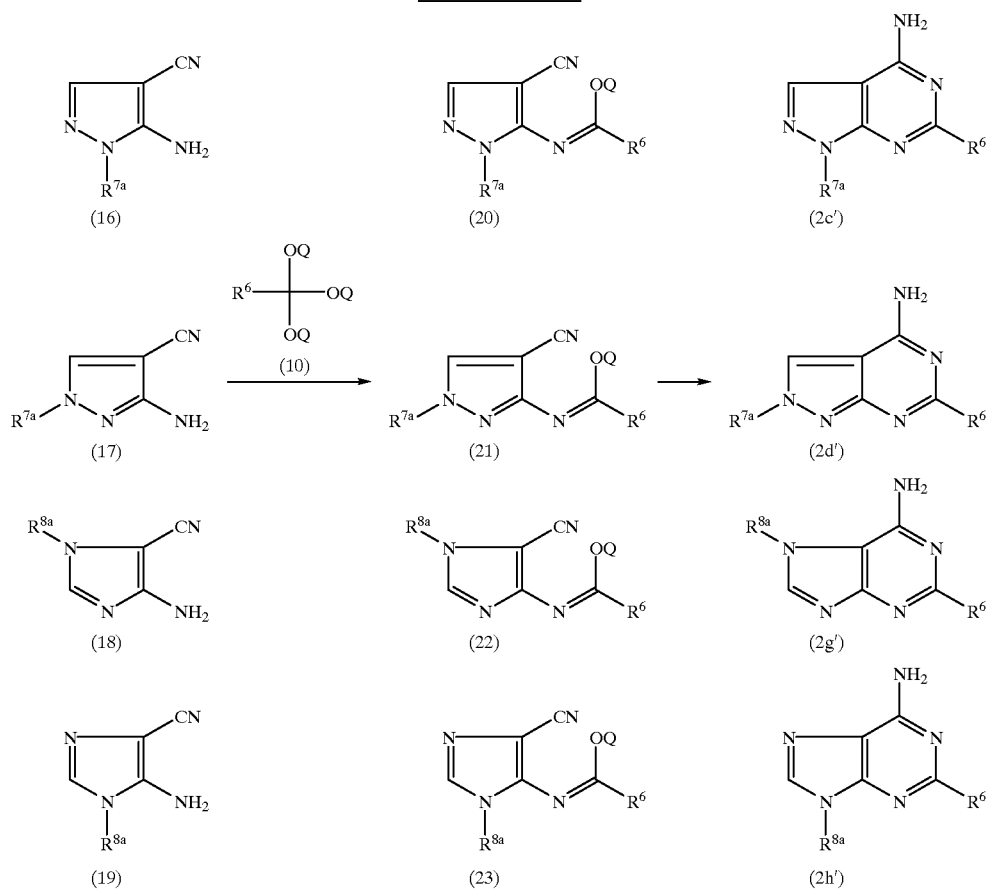

wherein $R^6$, $R^{7a}$, $R^{8a}$ and Q are as defined above.

In Reaction Scheme-5, the compounds (16)–(19) can be converted into compounds (20)–(23) by reaction with ortho-acid-ester (10). These compounds are then treated with ammonia to produce compounds (2c'), (2d'), (2g') and (2h'). The reactions can be carried out in a similar manner as the corresponding reactions shown in Reaction Scheme-3.

[Reaction Scheme-6]

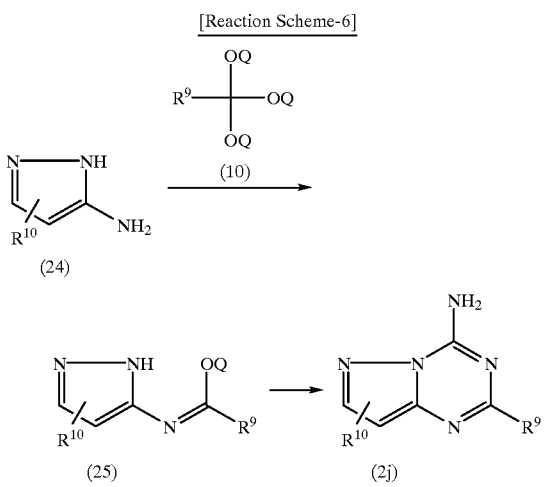

wherein Q is as defined above, $R^9$ is lower alkyl or phenyl and $R^{10}$ is hydrogen, lower alkyl, phenyl, phenyl(lower)alkyl or phenylthiophenyl.

The reaction of the compound (24) with ortho-acid-ester (10) in Reaction Scheme-6 can be carried out in a similar manner as the corresponding reaction shown in Reaction Scheme-3.

The compound (25) obtained by the reaction is reacted with cyaminade in the presence of an inert solvent such as methanol, ethanol or ethylene glycol to produce a compound (2j). The reaction is carried out using 1 to 1.5 equivalent of cyanamide at about room temperature to reflux temperature and is completed in about 3 to 30 hours.

The above reaction can be carried out by a single step. For example, about 1 equivalent each of ortho-acid ester (10) and cyanamide are added to a solution of the compound (24) in an inert solvent (e.g., methanol, ethanol or ethylene glycol) and the reaction is carried out at room temperature to reflux temperature for about 5 to 30 hours.

[Reaction Scheme-7]

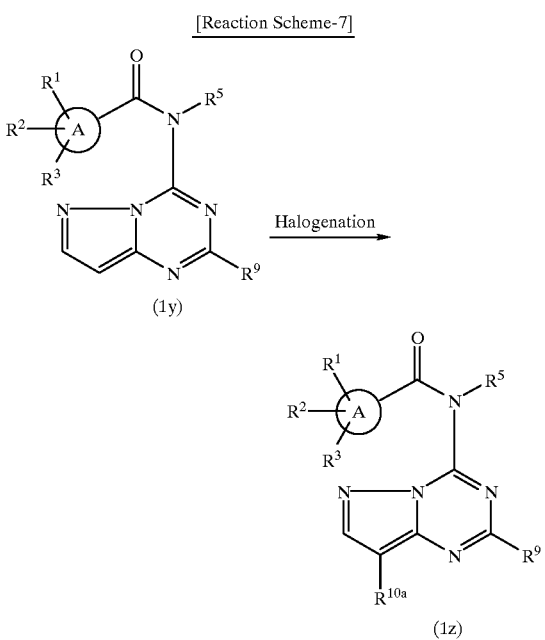

wherein A, $R^1$, $R^2$, $R^3$, $R^5$ and $R^9$ are as defined above, and $R^{10a}$ is a halogen atom.

The halogenation of the compound (1y) shown in Reaction Scheme-7 can be carried out in an inert solvent such as benzene, carbon tetrachloride, 1,2-dimethoxyethane or water using a halogenating agent such as N-bromosuccinimide (NBS), N-chlorosuccinimide or bromine. The halogenating agent is generally used in an amount of 1 equivalent to a slightly excessive amount relative to the compound (1y). The reaction is carried out at 0° C. to room temperature for about 15 minutes to 3 hours, thus proving a compound (1z).

[Reaction Scheme-8]

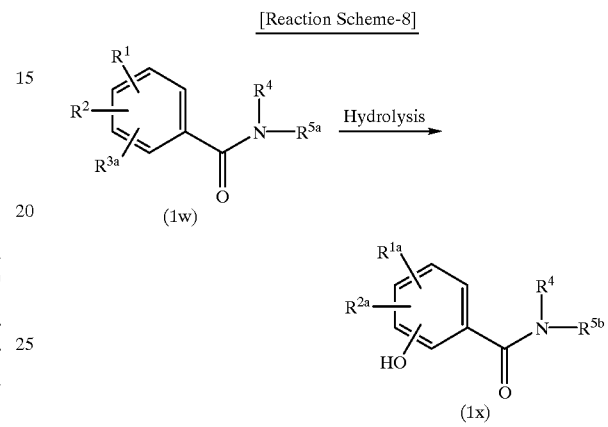

wherein $R^1$, $R^2$ and $R^4$ are as defined above, $R^{3a}$ is lower alkanoyloxy, $R^{1a}$ and $R^{2a}$ are the same or different and independently represent hydrogen, lower alkoxy, halogen, nitro, lower alkyl, halogen-substituted lower alkyl, phenyl, phenoxy, hydroxy, lower alkylthio, lower alkylsulfinyl or lower alkylsulfonyl, $R^{5a}$ is hydrogen or a group represented by

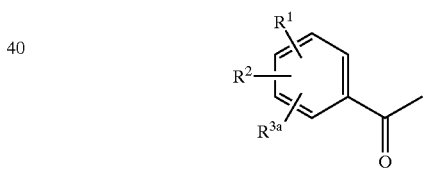

wherein $R^1$, $R^2$ and $R^{3a}$ are as defined above, and $R^{5b}$ is hydrogen or a group represented by

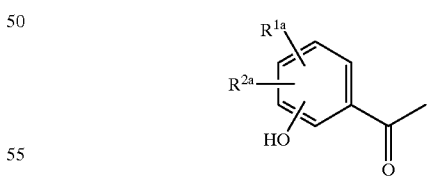

wherein $R^{1a}$ and $R^{2a}$ are as defined above.

The compound (1w) of the invention can be converted into the compound (1x) of the invention by hydrolysis. The hydrolysis can be carried out by treating the compound (1w) with aqueous NaOH solution, aqueous KOH solution or the like in an inert solvent such as methanol or ethanol. In this reaction, the reaction temperature is generally selected from the range of 0° C. to room temperature and reaction time from about 10 minutes to 3 hours.

[Reaction Scheme-9]

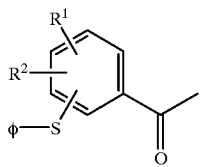
(1u)

Oxidation →

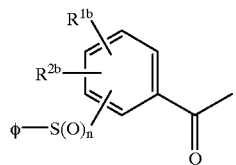
(1v)

wherein $R^1$, $R^2$ and $R^4$ are as defined above, φ is lower alkyl, n is 1 or 2, $R^{1b}$ and $R^{2b}$ are the same or different and independently represent hydrogen, lower alkoxy, halogen, nitro, lower alkyl, halogen-substituted lower alkyl, phenyl, phenoxy, lower alkanoyloxy, hydroxy, lower alkylthio, lower alkylsulfinyl or lower alkylsulfonyl, $R^{5c}$ represents hydrogen or a group represented by wherein $R^{1b}$, $R^{2b}$, n and φ are as defined above, and $R^{5d}$ is hydrogen or a group represented by wherein $R^{1b}$, $R^{2b}$, n and φ are as defined above.

The oxidation reaction of the compound (1u) can be carried out in an inert solvent such as acetic acid, dichloromethane or carbon tetrachloride using an oxidizing agent such as hydrogen peroxide, m-chloroperbenzoic acid or sodium periodate. To provide lower alkylsulfinyl (n=1) by oxidation, the oxidizing agent is used in an equimolar to slightly excessive amount relative to the starting compound and the reaction is carried out at about 0° C. to room temperature for about 15 minutes to 10 hours. To provide lower alkylsulfonyl (n=2), the oxidation reaction is carried out at about 0° C. to reflux temperature for about 15 minutes to 10 hours, using the oxidizing agent in an amount of at least 2 equivalents relative to the starting compound and optionally using a catalyst such as sodium tungstenate.

The objective compound (1v) wherein n=2 (sulfonyl compound) can also be obtained by re-oxidizing the above obtained compound wherein n=1 (sulfinyl compound) under any of the two reaction conditions.

The objective compounds in the steps of the above Reaction Schemes can be easily isolated and purified by conventional separation means, such as adsorption chromatography, preparative thin-layer chromatography, recrystallization, solvent extraction and the like.

The compounds of the invention can be converted into pharmaceutically acceptable acid addition salts, which are also included in the scope of the invention. Examples of useful acids to form such salts are hydrochloric acid, hydrobromic acid, sulfuric acid and like inorganic acids; and oxalic acid, fumaric acid, maleic acid, tartaric acid, citric acid, p-toluenesulfonic acid and like organic acids. The reaction for forming such an acid addition salt can be carried out by a conventional method.

The compounds of the invention wherein $R^5$ is hydrogen can be converted, by conventional methods, to sodium salts, potassium salts or like alkali metal salts, calcium salts, magnesium salts or like alkali earth metal salts, other copper salts, etc. These salts are also included in the scope of the invention.

Of the compounds of the invention, the compounds (1a) and (1b) may have resonance structures (1c)–(1e) and (1f)–(1h) shown below and thus can be represented by any of these formulas.

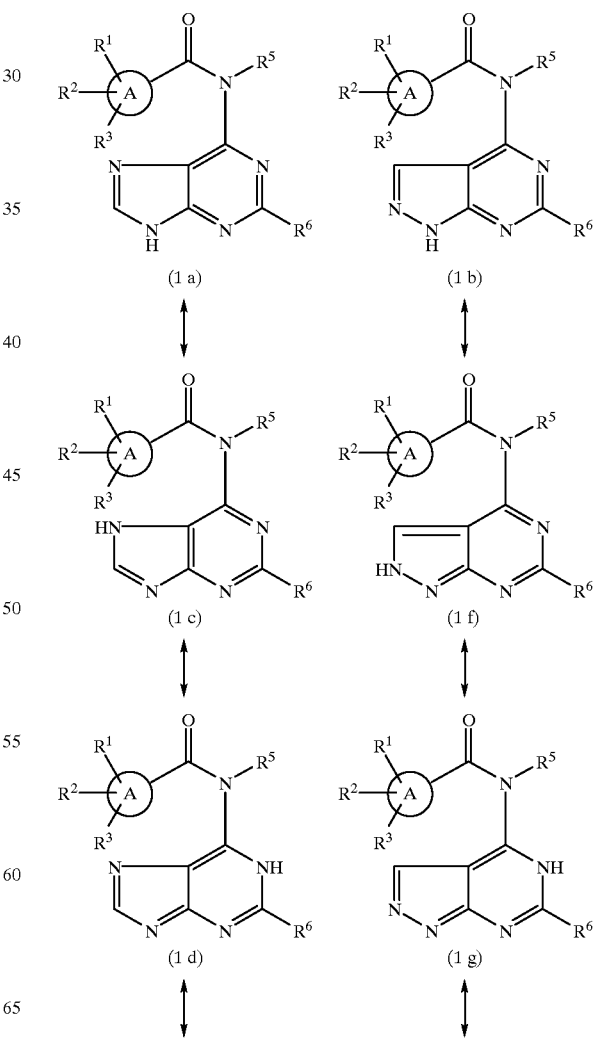

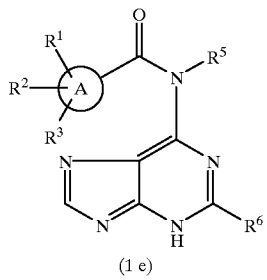
(1 e)

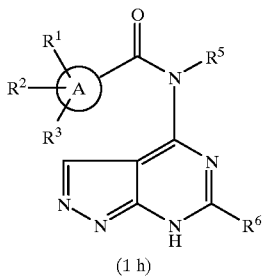
(1 h)

The compounds of the invention are made into general dosage forms of pharmaceutical compositions using suitable pharmaceutically acceptable carriers. Examples of useful pharmaceutically acceptable carriers are conventional diluents or excipients such as fillers, volume builders, binders, humectants, disintegrators, surfactants, lubricants and the like. Carriers for use are suitably selected according to the desired unit dosage forms.

A suitable unit dosage form can be selected from a wide variety of forms according to the intended medical treatment. Typical examples are tablets, pills, powders, solutions, suspensions, emulsions, granules, capsules, suppositories, injections (solutions, suspensions, etc.), ointments and the like.

The tablets can be molded using, as pharmaceutically acceptable carriers, excipients such as lactose, sucrose, sodium chloride, glucose, urea, starch, calcium carbonate, kaolin, crystalline cellulose, silicic acid and potassium phosphate; binders such as water, ethanol, propanol, simple syrup, glucose syrup, starch solution, gelatin solution, carboxymethyl cellulose, hydroxypropyl cellulose, methyl cellulose and polyvinyl pyrrolidone; disintegrators such as sodium carboxymethyl cellulose, calcium carboxymethyl cellulose, low-substituted hydroxypropyl cellulose, dry starch, sodium alginate, agar powder, laminaran powder, sodium hydrogen-carbonate and calcium carbonate; surfactants such as polyoxyethylene sorbitan fatty acid esters, sodium lauryl sulfate and stearyl monoglyceride; disintegration inhibitors such as sucrose, stearin, cacao butter and hydrogenated oil; absorption promoters such as quaternary ammonium base and sodium lauryl sulfate; humectants such as glycerin and starch; adsorbents such as starch, lactose, kaolin, bentonite and colloidal silicic acid; and lubricants such as purified talc, stearic acid salt, boric acid powder and polyethylene glycol.

If necessary, the tablets can further be coated with usual coating film to make them into sugar-coated tablets, gelatin-coated tablets, enteric tablets, film-coated tablets, double-layered tablets or multiple-layered tablets.

The pills can be made using, as pharmaceutically acceptable carriers, excipients such as glucose, lactose, starch, cacao butter, hydrogenated vegetable oil, kaolin and talc; binders such as gum arabic powder, tragacanth powder, gelatin and ethanol; and disintegrators such as laminaran and agar.

The suppositories can be molded using, as pharmaceutically acceptable carriers, polyethylene glycol, cacao butter, higher alcohols or their esters, gelatin, semisynthetic glycerides and the like.

The capsules are usually manufactured in a conventional manner by blending the compound of the invention with pharmaceutically acceptable carriers as mentioned above and encapsulating the mixture into hard gelatin capsule shells, soft capsule shells, etc.

When the compound of the invention is to be provided in an injectable form such as solution, emulsion or suspension, the preparation is preferably sterilized and rendered isotonic with respect to the blood. As the diluent for use in such a preparation, water, ethyl alcohol, macrogols, propylene glycol, ethoxylated isostearyl alcohol, polyoxyisostearyl alcohol, polyoxyethylene sorbitan fatty acid esters, etc. can be mentioned. In this operation, a sufficient amount of sodium chloride, glucose, glycerin or the like may be added to the pharmaceutical composition to provide an isotonic solution. Conventional solubilizers, buffers, anesthetics, etc. may also be added.

Further, coloring agents, preservatives, aromatics, flavors, sweeteners or other medicines may be optionally incorporated in the pharmaceutical composition.

The ointments in the form of pastes, creams, gels, etc. can be manufactured using diluents such as white vaseline, paraffin, glycerin, cellulose derivatives, polyethylene glycol, silicone and bentonite.

The proportion of the compound of the invention (as an active ingredient compound) in the pharmaceutical composition is not critical and can be selected from a broad range. It is generally preferable that the compound account for about 1 to 70 weight % of the final composition.

There is no limitation on methods for administering the pharmaceutical compositions of the invention. Thus, a proper method can be selected according to the dosage form, patient's age, sex and other conditions, severity of disease, etc. For example, the tablets, pills, solutions, suspensions, emulsions, granules and capsules are administered by the oral route. The injections are administered singly or in admixture with glucose, amino acid or like conventional infusions by the intravenous route or, if necessary, administered singly by the intramuscular, intradermal, subcutaneous or intraperitoneal route. The suppositories are administered intrarectally.

The dosage of the pharmaceutical composition is suitably selected according to the intended use, patient's age, sex and other conditions, severity of disease, etc. The dosage of the compound of the invention as the active ingredient is preferably about 0.5–20 mg per kg body weight a day, and this amount can be administered once or in 2–4 divided doses a day.

BEST MODE FOR CARRYING OUT THE INVENTION

The present invention will be described below in more detail with reference to Reference Examples and Examples. Preparation examples of the starting compounds for the compounds of the invention are shown as Reference Examples, and preparation examples of the compounds of the inventions as Examples.

REFERENCE EXAMPLE 1

Preparation of 4-amino-2-n-butylthieno[3,2-d]pyrimidine 3.8 ml of n-pentanoic acid chloride was added to 50 ml of an anhydrous pyridine solution containing 5.0 g of methyl 3-aminothiophene-2-carboxylate at 0° C. The mixture was stirred at 0° C. for 1 hour and further stirred at room temperature for 2 hours. The reaction mixture was concentrated, diluted with ethyl acetate and washed with 1N chloric acid, saturated aqueous sodium bicarbonate solution and saturated aqueous sodium chloride solution in this order. Ethyl acetate was distilled off under reduced pressure and the residue was purified by silica gel column chromatography (elution with n-hexane:ethyl acetate=5:1) to provide 7.0 g of methyl 3-pentanoylaminothiophene-2-carboxylate as a colorless oily compound.

To 5 ml of a dimethoxyethane solution containing 4.0 g of the compound obtained above was added 20 ml of 25% ammonia water. The mixture was sealed in a tube and heated at 100° C. for 24 hours. The reaction mixture was concentrated under reduced pressure and extracted with dichloromethane. The organic layer was collected and concentrated under reduced pressure. The crude crystals obtained were recrystallized from dichloromethane-n-hexane to provide 1.35 g of 5-n-butyl-7-hydroxythieno[3,2-d]pyrimidine as colorless crystals.

To 14 ml of a toluene solution containing 1.35 g of -the crystals obtained were added 2.4 ml of phosphorus oxychloride and 1.3 ml of triethylamine. The mixture was stirred at 115° C. for 12 hours. The reaction mixture was concentrated under reduced pressure, poured into ice water and neutralized with sodium acetate and filtered through Celite. The filtrate was extracted with ethyl acetate. The organic layer was collected, washed with water and then with saturated aqueous sodium chloride solution and concentrated under reduced pressure. The residue was purified by silica gel column chromatography (elution with n-hexane:ethyl acetate=4:1) to provide 1.4 g of 5-n-butyl-7-chlorothieno[3,2 -d]pyrimidine as a colorless oily compound.

To 3 ml of a dimethoxyethane solution containing 1.4 g of the oily compound obtained was added 15 ml of 25% ammonia water. The mixture was sealed in a tube and heated at 80° C. for 20 hours. After completion of the reaction, the reaction mixture was cooled with water. The crystals precipitated were collected by filtration, washed with water and then dried to provide 1.2 g of the objective compound as colorless crystals. 4-Amino-2-n-propylthieno[3,2-d] pyrimidine was prepared in a similar manner as above.

REFERENCE EXAMPLE 2

Preparation of 4-amino-6-n-butyl-1H-pyrazolo[3,4-d]pyrimidine

To 50 ml of an anhydrous DMF solution containing 5 g of 3-amino-4-cyanopyrazole was added 12 ml of trimethyl ortho-n-pentanoate. The mixture was stirred at 90° C. for 20 minutes. The reaction mixture was diluted with ethyl acetate, washed with water and then with saturated aqueous sodium chloride solution and concentrated under reduced pressure. The residue was purified by silica gel column chromatography (elution with n-hexane:ethyl acetate=2:1) to provide 6.5 g of 4-cyano-3-[N-(1-methoxypentylidene)amino]pyrazole as a colorless oily compound.

To 6.5 g of the compound obtained above was added 50 ml of a methanol solution of ammonia (about 7%). The mixture was stirred at room temperature for 36 hours. After completion of the reaction, the reaction mixture was concentrated under reduced pressure and the residue was recrystallized from ethanol-n-hexane to provide 4.1 g of the objective compound as colorless crystals.

REFERENCE EXAMPLE 3

Preparation of 4-amino-2-benzyloxycarbonyl-6-n-butyl-2H-pyrazolo[3,4-d]pyrimidine To 7.5 ml of an anhydrous DMF solution containing 750 mg of the compound obtained in Reference Example 2 were added 1.1 ml of triethylamine and 3.4 ml of benzyloxycarbonyl chloride (about 30% toluene solution) at 0° C., followed by stirring at 0° C. for 1 hour. The reaction mixture was poured into ice water, and the crystals precipitated were collected by filtration and washed with diethyl ether. The crude crystals were purified by silica gel column chromatography (elution with chloroform:methanol=40:11→10:1) and recrystallized from ethanol-n-hexane to provide 390 mg of the objective compound as colorless crystals.

REFERENCE EXAMPLES 4 AND 5

Preparation of 4-amino-2-benzyl-6-n-butyl-2H-pyrazolo[3,4-d]pyrimidine and 4-amino-1-benzyl-6-n-butyl- 1H-pyrazolo[3,4-d]pyrimidine Using the compound obtained in Reference Example 2, benzyl bromide and sodium hydride as a base, the procedure was carried out in a similar manner as in Reference Example 3. The crude product obtained was recrystallized from dichloromethane-diethyl ether to provide 4-amino-2-benzyl-6-n-butyl-2H-pyrazolo[3,4-d]pyrimidine as colorless crystals.

On the other hand, the mother liquor of recrystallization was concentrated and the residue was purified by column chromatography (elution with n-hexane:ethyl acetate=2:3) and further recrystallized from diethyl ether-n-hexane to provide 4-amino-1-benzyl-6-n-butyl-1H-pyrazolo[3,4-d] pyrimidine as colorless crystals.

REFERENCE EXAMPLE 6

Preparation of 6-amino-2-n-butyl-9H-purine

To 24 ml of an anhydrous DMF solution containing 10 g of 4-amino-5-cyanoimidazole was added 24 ml of trimethyl ortho-n-pentanoate. The mixture was stirred at 90° C. for 20 minutes. The reaction mixture was concentrated under reduced pressure, and the residue was purified by silica gel column chromatography (elution with ethyl acetate) and recrystallized from ethyl acetate-n-hexane to provide 17.7 g of 5-cyano-4-[N-(1-methoxypentylidene)amino]imidazole as colorless crystals.

To 15 g of the compound obtained above was added 100 ml of a methanol solution of ammonia (2N). The mixture was stirred at room temperature for 6 days. After completion of the reaction, the crystals precipitated were collected, washed with methanol and dried to provide 9.5 g of the objective compound as colorless crystals. The filtrate was concentrated and the residue was recrystallized from ethanol-n-hexane to provide 3.0 g of the objective compound as colorless crystals.

REFERENCE EXAMPLE 7

Preparation of 6-amino-9-benzyloxycarbonyl-2-n-butyl-9H-purine

To 100 ml of an anhydrous DMF solution containing 10 g of the compound obtained in Reference Example 6 were added 22 ml of triethylamine and 45 ml of benzyloxycarbonyl chloride (about 30% toluene solution) at 0° C., followed by stirring at 0° C. for 5 hours. The reaction mixture was poured into ice water and extracted with chloroform. The chloroform layer was washed with saturated aqueous sodium chloride solution and concentrated under reduced pressure. The residue was recrystallized from chloroform-diethyl ether to provide 8.5 g of the objective compound as a colorless crystals. The mother liquor was concentrated and the residue was purified by silica gel column chromatography (elution with

REFERENCE EXAMPLE 8

Preparation of 6-amino-1-benzyl-2-n-butyl-1H-purine 5 g of 5-cyano-4-[N-(1-methoxypentylidine)amino]imidazole obtained in Reference Example 6 was dissolved in 50 ml of methanol, and 3.2 ml of benzylamine was added. The mixture was stirred at 50° C. for 2 hours and allowed to stand for cooling. The crystals precipitated were collected by filtration and washed with diethyl ether to provide 6.2 g of the objective compound as colorless crystals.

REFERENCE EXAMPLE 9

Preparation of 6-amino-2-n-butyl-1-methyl-1H-purine

The procedure was carried out in a similar manner as in Reference Example 8 to provide the objective compound as colorless crystals.

REFERENCE EXAMPLE 10

Preparation of 6-amino-7-benzyl-2-n-butyl-7H-purine

Using 1-benzyl-4-amino-5-cyanoimidazole, the procedure was carried out in a similar manner as in Reference Example 6. The objective compound was obtained as colorless crystals.

REFERENCE EXAMPLE 11

Preparation of 6-amino-9-benzyl-2-n-butyl-9H-purine

Using 3-benzyl-4-amino-5-cyanoimidazole, the procedure was carried out in a similar manner as in Reference Example 6. The objective compound was obtained as colorless crystals.

REFERENCE EXAMPLE 12

Preparation of 4-amino-2-n-butylpyrazolo[1,5-a]-1,3,5-triazine

To 250 ml of an anhydrous DMF solution of 50 g of 3-aminopyrazole was added 120 ml of trimethyl ortho-n-pentanoate, followed by stirring at 70° C. for 22 hours. After completion of the reaction, the reaction mixture was concentrated under reduced pressure and the residue was purified by silica gel column chromatography (elution with dichloromethane:methanol=50:1→20:1) to provide 60 g of 3-[N-(1-methoxypentylidene)amino]pyrazole as a colorless oily compound.

The above obtained compound, 60 g, was dissolved in 300 ml of methanol, followed by addition of 15.3 g of cyanamide. The mixture was stirred at 60° C. for 17 hours. After completion of the reaction, the reaction mixture was concentrated under reduced pressure and the residue was purified by silica gel column chromatography (elution with dichloromethane:methanol=50:1), and further recrystallized from diisopropyl ether to provide 36.4 g of the objective compound as colorless crystals. The mother liquor of recrystallization was purified in a similar manner as above to provide 7 g of the objective compound as crystals.

chloroform:methanol=20:1) and recrystallized from chloroform-diethyl ether to provide 2.4 g of the objective compound as colorless crystals.

REFERENCE EXAMPLE 13

Preparation of 4-amino-2-phenylpyrazolo[1,5-a]-1,3,5-triazine

The procedure was carried out in a similar manner as in Reference Example 12 to provide the objective compound as colorless crystals.

REFERENCE EXAMPLES 14–20

The procedure was carried out in a similar manner as in Reference Example 12 to provide the following compounds as crystals.

REFERENCE EXAMPLE 14

4-Amino-2-methylpyrazolo[1,5-a]-1,3,5-triazine

REFERENCE EXAMPLE 15

4-Amino-2-ethylpyrazolo[1,5-a]-1,3,5-triazine

REFERENCE EXAMPLE 16

4-Amino-2-n-propylpyrazolo[1,5-a]-1,3,5-triazine

REFERENCE EXAMPLE 17

4-Amino-2-n-pentylpyrazolo[1,5-a]-1,3,5-triazine

REFERENCE EXAMPLE 18

4-Amino-2-benzylpyrazolo[1,5-a]-1,3,5-triazine

REFERENCE EXAMPLE 19

4-Amino-2-n-butyl-8-phenylpyrazolo[1,5-a]-1,3,5-triazine

REFERENCE EXAMPLE 20

4-Amino-2-n-butyl-8-(4-phenylthiophenyl)pyrazolo[1,5-a]-1,3,5-triazine

EXAMPLE 1

Preparation of N-(2-n-butylthieno[3,2-d]pyrimidin-4-yl)-3,4,5-trimethoxybenzamide To 4 ml of an anhydrous pyridine solution containing 200 mg of the compound obtained in Reference Example 1 was added 270 mg of 3,4,5-trimethoxybenzoyl chloride at 0° C. The mixture was stirred at 0° C. for 1 hour and further stirred at room temperature for 3 days. The reaction mixture was diluted with chloroform, washed with 10% hydrochloric acid, saturated aqueous sodium bicarbonate solution and saturated aqueous sodium chloride solution in this order and concentrated under reduced pressure. The residue was purified by silica gel column chromatography (elution with n-hexane:ethyl acetate=3:2), and further recrystallized from n-hexane to provide 160 mg of the objective compound as colorless crystals. Table 1 shows the structure and melting point of the compound obtained.

EXAMPLES 2–8

The compounds set forth in Table 1 were prepared in a similar manner as in Example 1. Table 1 shows the structures and melting points of the compounds obtained. As regards the oily compounds, $^1$H-NMR spectral data (δ: ppm; solvent: $CDCl_3$; inner standard: tetramethylsilane) are shown.

EXAMPLE 9

Preparation of N-(2-n-butyl-9H-purin-6-yl)-3,4,5-trimethoxybenzamide

To 50 ml of an anhydrous pyridine solution containing 5 g of the compound obtained in Reference Example 7 was added 5.3 g of 3,4,5-trimethoxybenzoyl chloride at 0° C. The mixture was stirred at 0° C. for 2 hours and further stirred at room temperature for 5 days. The reaction mixture was diluted with chloroform, washed with 10% hydrochloric acid and then with 5% aqueous sodium hydroxide solution. The aqueous layer was collected, neutralized with 10% hydrochloric acid and extracted with chloroform. The chloroform layer was collected, washed with water and then with saturated aqueous sodium chloride solution and concentrated under reduced pressure. The residue was purified by silica gel column chromatography (elution with chloroform:methanol=50:1→20:1) and recrystallized from dichloromethanediethyl ether to provide 2.7 g of the objective compound as colorless crystals. Table 1 shows the structure and melting point of the compound obtained.

EXAMPLE 10

Preparation of N-(6-n-butyl-1H-pyrazolo[3,4-d]pyrimidin-4-yl)-3,4,5-trimethoxybenzamide To 2 ml of an anhydrous pyridine solution containing 100 mg of the compound obtained in Reference Example 3 was added 106 mg of 3,4,5-trimethoxybenzoyl chloride at 0° C. The mixture was stirred at 0° C. for 1 hour and further stirred at room temperature for 1 hour. The reaction mixture was diluted with ethyl acetate, washed with 10% hydrochloric acid, saturated aqueous sodium bicarbonate solution and saturated aqueous sodium chloride solution in this order and then concentrated under reduced pressure. The residue was purified by silica gel column chromatography (elution with chloroform:ethyl acetate=1:1) and further recrystallized from dichloromethane-n-hexane to provide 150 mg of colorless crystals.

The crystals obtained were dissolved in 10 ml of ethanol, and 20 mg of 10% palladium-carbon was added. In a hydrogen gas atmosphere, the mixture was stirred at room temperature overnight. Palladium-carbon was filtered off using Celite, and the filtrate was concentrated under reduced pressure. The residue was purified by silica gel column chromatography (elution with chloroform:methanol=50:1) and further recrystallized from ethyl acetate-n-hexane to provide 60 mg of the objective compound as colorless crystals. Table 1 shows the structure and melting point of the compound obtained.

EXAMPLES 11 AND 12

Preparation of N-(9-benzyl-2-n-butyl-9H-purin-6-yl)-3,4,5-trimethoxybenzamide and N-(9-benzyl-2-n-butyl-9H-purin-6-yl)-N-(3,4,5-trimethoxybenzoyl)-3,4,5-trimethoxybenzamide To 30 ml of an anhydrous pyridine solution containing 1.5 g of the compound obtained in Reference Example 11 was added 1.85 g of 3,4,5-trimethoxybenzoyl chloride at room temperature. The mixture was stirred at room temperature for 6 days. The reaction mixture was diluted with dichloromethane, washed with 10% hydrochloric acid, saturated aqueous sodium bicarbonate solution, water and saturated aqueous sodium chloride solution in this order and then concentrated under reduced pressure. The residue was purified by silica gel column chromatography (elution with dichloromethane:methanol=100: 150:1). The former fraction was recrystallized from n-hexane to provide 0.75 g of N-(9-benzyl-2-n-butyl-9H-purin-6-yl)-N-(3,4,5-trimethoxybenzoyl)-3,4,5-trimethoxybenzamide as colorless crystals. The latter fraction was recrystallized from n-hexane to provide 0.72 g of N-(9-benzyl-2-n-butyl-9H-purin-6-yl)-3,4,5-trimethoxybenzamide as colorless crystals. Table 1 shows the structures and melting points of the compounds obtained.

TABLE 1

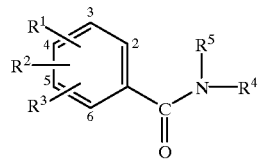

Me = Methyl group, n-Bu = n-Butyl group, Ph = Phenyl group

| Example | $R^1$ | $R^2$ | $R^3$ | $R^4$ | $R^5$ | Melting Point (° C.) |
|---|---|---|---|---|---|---|
| 1 | 3-OMe | 4-OMe | 5-OMe | 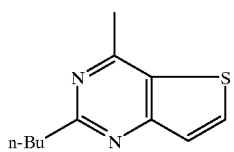 | H | 95–97 |

TABLE 1-continued

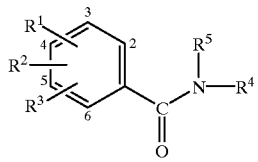

Me = Methyl group, n-Bu = n-Butyl group, Ph = Phenyl group

| Example | R¹ | R² | R³ | R⁴ | R⁵ | Melting Point (° C.) |
|---|---|---|---|---|---|---|
| 2 | 3-OMe | 4-OMe | 5-OMe | 6-methyl-2-n-butyl-7-benzyl-7H-purine | H | 185–187 |
| 3 | 3-OMe | 4-OMe | 5-OMe | 6-methyl-2-n-butyl-1-benzyl-1H-purine | H | Oil $^1$H-NMR |
| 4 | 3-OMe | 4-OMe | 5-OMe | 6-methyl-2-n-butyl-1-methyl-1H-pyrazolo | H | 159–161 |
| 5 | 3-OMe | 4-OMe | 5-OMe | 4-methyl-6-n-butyl-2-benzyl-pyrazolo[3,4-d]pyrimidine | H | 217–219 Hydrochloride |
| 6 | 3-OMe | 4-OMe | 5-OMe | 4-methyl-6-n-butyl-1-benzyl-pyrazolo[3,4-d]pyrimidine | H | 46–48 |
| 7 | 3-OMe | 4-OMe | 5-OMe | 4-methyl-2-n-butyl-pyrazolo[1,5-a][1,3,5]triazine | H | 124–126 |
| 8 | 3-OMe | 4-OMe | 5-OMe | 4-methyl-2-phenyl-pyrazolo[1,5-a][1,3,5]triazine | H | 174–176 |

TABLE 1-continued

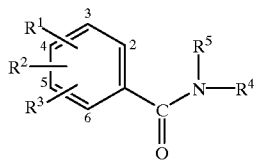

Me = Methyl group, n-Bu = n-Butyl group, Ph = Phenyl group

| Example | $R^1$ | $R^2$ | $R^3$ | $R^4$ | $R^5$ | Melting Point (° C.) |
|---|---|---|---|---|---|---|
| 9 | 3-OMe | 4-OMe | 5-OMe | 6-methyl-2-n-butyl-purine (NH) | H | 132–134 |
| 10 | 3-OMe | 4-OMe | 5-OMe | 4-methyl-6-n-butyl-pyrazolo[3,4-d]pyrimidine (NH) | H | 151–153 |
| 11 | 3-OMe | 4-OMe | 5-OMe | 6-methyl-2-n-butyl-9-benzyl-purine | H | 92–94 |
| 12 | 3-OMe | 4-OMe | 5-OMe | 6-methyl-2-n-butyl-9-benzyl-purine | 3,4,5-trimethoxybenzoyl | 112–114 |

$^1$H-NMR data on the compound of Example 3 shown in Table 1 are presented below.

0.90 (3H, t, J=7.2), 1.3–1.5 (2H, m),
1.8–1.9 (2H, m), 2.87 (2H, t, J=7.7),
3.62 (6H, s), 3.86 (3H, s), 5.6–6.2 (2H, brs),
7.18 (2H, d, J=6.9), 7.2–7.4 (5H, m),
8.13 (1H, s), 12.3–12.5 (1H, brs).

EXAMPLES 13–53

The compounds set forth in Table 2 were prepared in a similar manner as in Example 1. Table 2 shows the structures and melting points of the compounds obtained. As regards the oily compounds, $^1$H-NMR spectral data (5: ppm; solvent: DMSO-d$_6$; inner standard: tetramethylsilane) are shown.

EXAMPLE 54

Preparation of N-(2-n-butylpyrazolo[1,5-a]-1,3,5-triazin-4-yl)-2-methylsulfinylbenzamide To 18 ml of an acetic acid solution containing 1.2 g of the compound obtained in Example 47 was added 0.44 ml of 30% aqueous hydrogen peroxide solution. The mixture was stirred at room temperature for 4 hours. After completion of the reaction, the reaction mixture was neutralized with 10% aqueous sodium hydroxide solution and extracted with dichloromethane. The organic layer was collected, washed with water and then with saturated aqueous sodium chloride solution and concentrated under reduced pressure. Diethyl ether was added to the residue and the crystals precipitated were collected by filtration. The crude crystals were recrystallized from dichloromethane-diethyl ether to provide 0.48 g of the objective compound as colorless crystals. Table 2 shows the structure and melting point of the compound obtained.

EXAMPLE 55

Preparation of N-(2-n-butylpyrazolo[1,5-a]-1,3,5-triazin-4-yl)-2-methylsulfonylbenzamide To 10 ml of a chloroform solution containing 1.0 g of the compound obtained in Example 54 was added dropwise 15 ml of a chloroform solution containing 1.44 g of methachloroperbenzoate at −78° C. The mixture was stirred at −78° C. for 45 minutes and further stirred at 0° C. for 1 hour. The reaction mixture was diluted with dichloromethane, washed with aqueous sodium bicarbonate solution and then with saturated aqueous sodium chloride solution and concentrated under reduced pressure. The residue was purified by silica gel column chromatography (elution; chloroform→chloroform:methanol=40:1) and recrystallized from ethyl acetate-n-hexane to provide 0.95 g of the objective compound as colorless crystals. Table 2 shows the structure and melting point of the compound obtained.

EXAMPLE 56

Preparation of N-(2-n-butylpyrazolo[1,5-a]-1,3,5-triazin-4-yl)-2-hydroxybenzamide To 15 ml of an ethanol suspension containing 1.5 g of the compound obtained in Example 44 was added 2.0 ml of 10% aqueous sodium hydroxide solution at 0° C. The mixture was stirred at 0° C. for 1 hour. To the reaction mixture were added 2.2 ml of 10% hydrochloric acid and 80 ml of water. The crystals precipitated were collected by filtration, washed with water and recrystallized from 60% ethanol hydrate to provide 1.12 g of the objective compound as colorless crystals. Table 2 shows the structure and melting point of the compound obtained.

EXAMPLE 57

Preparation of N-(2-n-butylpyrazolo[1,5-a]-1,3,5-triazin-4-yl)-4-hydroxybenzamide Using the compound obtained in Example 46, the objective compound was prepared in a similar manner as in Example 56. Table 2 shows the structure and melting point of the compound obtained.

EXAMPLE 58

Preparation of N-(8-bromo-2-n-butylpyrazolo[1,5-a]-1,3,5-triazin-4-yl)-3,4, 5-trimethoxybenzamide 1.0 g of the compound obtained in Example 7 was dissolved in 20 ml of 1,2-dimethoxyethane-water (3:1). After addition of 0.51 g of NBS at 0° C., the mixture was stirred at 0° C. for 1 hour. The reaction mixture was diluted with water and the crystals precipitated were collected by filtration. The crude crystals obtained were washed with water and recrystallized from methanol- water to provide 0.94 g of the objective compound as colorless crystals. Table 2 shows the structure and melting point of the compound obtained.

EXAMPLES 59–62

The compounds shown as Examples 59–62 in Table 2 were isolated from the former fractions of silica gel column chromatography in Examples 7, 13, 14 and 25 respectively. Table 2 shows the structures and melting points of the compounds obtained.

TABLE 2

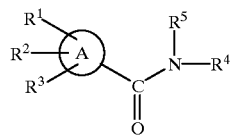

Me = Methyl group, Et = Ethyl group, n-Pr = n-Propyl group, n-Bu = n-Butyl group, t-Bu = t-Butyl group, n-Pe = n-Pentyl group, Ac = Acetyl group, Ph = Phenyl group

| Example | A | $R^1$ | $R^2$ | $R^3$ | $R^4$ | $R^5$ | Melting point (° C.) |
|---|---|---|---|---|---|---|---|
| 13 | phenyl | 2-CF$_3$ | H | H | 2-n-Bu-pyrazolo[1,5-a]-1,3,5-triazin-4-yl | H | >112 (decomposition) Na salt |
| 14 | phenyl | 2-Cl | H | H | 2-n-Bu-pyrazolo[1,5-a]-1,3,5-triazin-4-yl | H | >63 (decomposition) Na salt |
| 15 | phenyl | 2-Cl | 4-Cl | H | 2-n-Bu-pyrazolo[1,5-a]-1,3,5-triazin-4-yl | H | 100–102 |

TABLE 2-continued

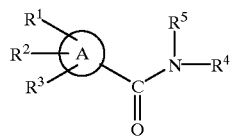

Me = Methyl group, Et = Ethyl group, n-Pr = n-Propyl group, n-Bu = n-Butyl group,
t-Bu = t-Butyl group, n-Pe = n-Pentyl group, Ac = Acetyl group, Ph = Phenyl group

| Example | A— | R¹ | R² | R³ | R⁴ | R⁵ | Melting point (° C.) |
|---|---|---|---|---|---|---|---|
| 16 | phenyl | 2-OMe | H | H | 4-methyl-2-n-Bu-pyrazolo-triazinyl | H | 119–121 |
| 17 | phenyl | 3-Cl | H | H | 4-methyl-2-n-Bu-pyrazolo-triazinyl | H | 116–118 |
| 18 | phenyl | 4-Cl | H | H | 4-methyl-2-n-Bu-pyrazolo-triazinyl | H | 74–76 |
| 19 | phenyl | 3-F | H | H | 4-methyl-2-n-Bu-pyrazolo-triazinyl | H | 96–98 |
| 20 | phenyl | H | H | H | 4-methyl-2-n-Bu-pyrazolo-triazinyl | H | 82–84 |
| 21 | phenyl | 3-OMe | H | H | 4-methyl-2-n-Bu-pyrazolo-triazinyl | H | 75–77 |
| 22 | phenyl | 4-OMe | H | H | 4-methyl-2-n-Bu-pyrazolo-triazinyl | H | 91–93 |

TABLE 2-continued

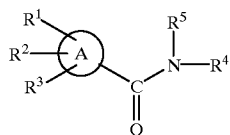

Me = Methyl group, Et = Ethyl group, n-Pr = n-Propyl group, n-Bu = n-Butyl group,
t-Bu = t-Butyl group, n-Pe = n-Pentyl group, Ac = Acetyl group, Ph = Phenyl group

| Example | A— | $R^1$ | $R^2$ | $R^3$ | $R^4$ | $R^5$ | Melting point (° C.) |
|---|---|---|---|---|---|---|---|
| 23 | phenyl | 2-Cl | 5-Cl | H | 4-methyl-2-n-Bu-pyrazolo[1,5-a][1,3,5]triazinyl | H | >134 (decomposition) Hydrochloride |
| 24 | phenyl | 2-Br | H | H | 4-methyl-2-n-Bu-pyrazolo[1,5-a][1,3,5]triazinyl | H | >135 (decomposition) Hydrochloride |
| 25 | phenyl | 2-NO$_2$ | H | H | 4-methyl-2-n-Bu-pyrazolo[1,5-a][1,3,5]triazinyl | H | 89–91 |
| 26 | phenyl | 3-OMe | 4-OMe | 5-OMe | 4-methyl-2-n-Bu-pyrazolo[1,5-a][1,3,5]triazinyl | H | 165–167 |
| 27 | phenyl | 3-OMe | 4-OMe | 5-OMe | 4-methyl-2-Et-pyrazolo[1,5-a][1,3,5]triazinyl | H | 148–150 |
| 28 | phenyl | 3-OMe | 4-OMe | 5-OMe | 4-methyl-2-n-Pr-pyrazolo[1,5-a][1,3,5]triazinyl | H | 145–147 |
| 29 | phenyl | 4-t-Bu | H | H | 4-methyl-2-n-Bu-pyrazolo[1,5-a][1,3,5]triazinyl | H | 96–98 |

TABLE 2-continued
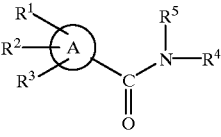
Me = Methyl group, Et = Ethyl group, n-Pr = n-Propyl group, n-Bu = n-Butyl group,
t-Bu = t-Butyl group, n-Pe = n-Pentyl group, Ac = Acetyl group, Ph = Phenyl group
| Example | A— | R¹ | R² | R³ | R⁴ | R⁵ | Melting point (° C.) |
|---|---|---|---|---|---|---|---|
| 30 | 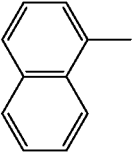 | H | H | H | 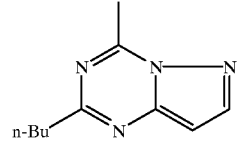 | H | 100–102 |
| 31 | 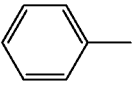 | 4-CF₃ | H | H | 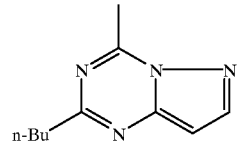 | H | 90–92 |
| 32 | 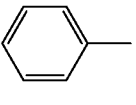 | 2-OMe | 4-OMe | H | 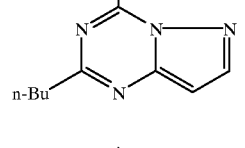 | H | 136–138 |
| 33 | 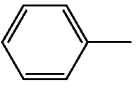 | 2-OMe | 3-OMe | 4-OMe | 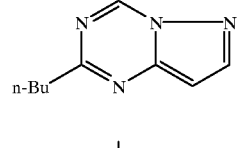 | H | 142–144 |
| 34 | 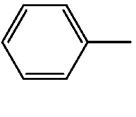 | 4-Ph | H | H | 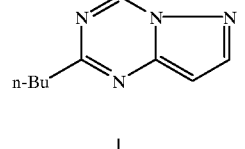 | H | 119–121 |
| 35 | 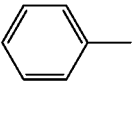 | 2-OPh | H | H | 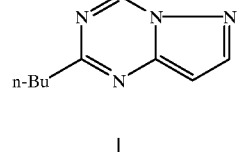 | H | 147–149 |
| 36 | 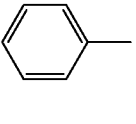 | 4-O-n-Bu | H | H | 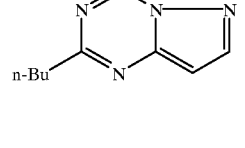 | H | 116–118 |

TABLE 2-continued

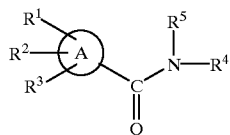

Me = Methyl group, Et = Ethyl group, n-Pr = n-Propyl group, n-Bu = n-Butyl group,
t-Bu = t-Butyl group, n-Pe = n-Pentyl group, Ac = Acetyl group, Ph = Phenyl group

| Example | A— | R¹ | R² | R³ | R⁴ | R⁵ | Melting point (° C.) |
|---|---|---|---|---|---|---|---|
| 37 | phenyl | 3-OMe | 4-OMe | 5-OMe | 4-methyl-pyrazolo[1,5-a][1,3,5]triazine | H | 213–215 |
| 38 | 3-pyridyl | H | H | H | 4-methyl-2-n-Bu-pyrazolo[1,5-a][1,3,5]triazine | H | 76–78 |
| 39 | 2-furyl | H | H | H | 4-methyl-2-n-Bu-pyrazolo[1,5-a][1,3,5]triazine | H | 100–102 |
| 40 | phenyl | 3-OMe | 4-OMe | 5-OMe | 4-methyl-2-n-Pe-pyrazolo[1,5-a][1,3,5]triazine | H | 115–117 |
| 41 | phenyl | 3-OMe | 4-OMe | 5-OMe | 4-methyl-2-PhCH₂-pyrazolo[1,5-a][1,3,5]triazine | H | 164–166 |
| 42 | phenyl | 3-OMe | 4-OMe | 5-OMe | 4-methyl-2-n-Bu-8-Ph-pyrazolo[1,5-a][1,3,5]triazine | H | 150–152 |
| 43 | phenyl | 2-Me | H | H | 4-methyl-2-n-Bu-pyrazolo[1,5-a][1,3,5]triazine | H | Oil ¹H-NMR |

TABLE 2-continued

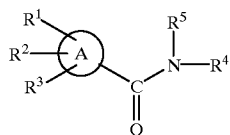

Me = Methyl group, Et = Ethyl group, n-Pr = n-Propyl group, n-Bu = n-Butyl group,
t-Bu = t-Butyl group, n-Pe = n-Pentyl group, Ac = Acetyl group, Ph = Phenyl group

| Example | A— | R¹ | R² | R³ | R⁴ | R⁵ | Melting point (° C.) |
|---|---|---|---|---|---|---|---|
| 44 | phenyl | 2-OAc | H | H | 4-methyl-2-n-Bu-pyrazolo[1,5-a][1,3,5]triazin-yl | H | 123–125 |
| 45 | phenyl | 3-Cl | 4-Cl | H | 4-methyl-2-n-Bu-pyrazolo[1,5-a][1,3,5]triazin-yl | H | 113–115 |
| 46 | phenyl | 4-OAc | H | H | 4-methyl-2-n-Bu-pyrazolo[1,5-a][1,3,5]triazin-yl | H | 140–142 |
| 47 | phenyl | 2-SMe | H | H | 4-methyl-2-n-Bu-pyrazolo[1,5-a][1,3,5]triazin-yl | H | 111–113 |
| 48 | phenyl | 2-OEt | H | H | 4-methyl-2-n-Bu-pyrazolo[1,5-a][1,3,5]triazin-yl | H | 153–155 |
| 49 | phenyl | 3-OMe | 4-OMe | H | 4-methyl-2-n-Bu-pyrazolo[1,5-a][1,3,5]triazin-yl | H | 113–115 |
| 50 | phenyl | 2-OMe | 3-OMe | H | 4-methyl-2-n-Bu-pyrazolo[1,5-a][1,3,5]triazin-yl | H | 147–149 |

TABLE 2-continued

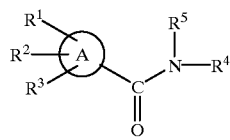

Me = Methyl group, Et = Ethyl group, n-Pr = n-Propyl group, n-Bu = n-Butyl group,
t-Bu = t-Butyl group, n-Pe = n-Pentyl group, Ac = Acetyl group, Ph = Phenyl group

| Example | A— | R¹ | R² | R³ | R⁴ | R⁵ | Melting point (° C.) |
|---|---|---|---|---|---|---|---|
| 51 | phenyl | 3-OMe | 4-OMe | 5-OMe | 4-methyl-2-n-Bu-7-Ph-pyrazolo[1,5-a][1,3,5]triazine | H | 172–174 |
| 52 | phenyl | 3-OMe | 4-OMe | 5-OMe | 4-methyl-2-n-Bu-8-(4-SPh-phenyl)-pyrazolo[1,5-a][1,3,5]triazine | H | 150–152 |
| 53 | phenyl | 3-Me | H | H | 4-methyl-2-n-Bu-pyrazolo[1,5-a][1,3,5]triazine | H | 76–78 |
| 54 | phenyl | 2-SOMe | H | H | 4-methyl-2-n-Bu-pyrazolo[1,5-a][1,3,5]triazine | H | 168–170 |
| 55 | phenyl | 2-SO₂Me | H | H | 4-methyl-2-n-Bu-pyrazolo[1,5-a][1,3,5]triazine | H | 105–107 |
| 56 | phenyl | 2-OH | H | H | 4-methyl-2-n-Bu-pyrazolo[1,5-a][1,3,5]triazine | H | 125–127 |

TABLE 2-continued

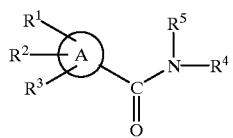

Me = Methyl group, Et = Ethyl group, n-Pr = n-Propyl group, n-Bu = n-Butyl group,
t-Bu = t-Butyl group, n-Pe = n-Pentyl group, Ac = Acetyl group, Ph = Phenyl group

| Example | A— | R¹ | R² | R³ | R⁴ | R⁵ | Melting point (° C.) |
|---|---|---|---|---|---|---|---|
| 57 | phenyl | 4-OH | H | H | 4-methyl-2-n-butyl-pyrazolo[1,5-a][1,3,5]triazine | H | 169–171 |
| 58 | phenyl | 3-OMe | 4-OMe | 5-OMe | 4-methyl-2-n-butyl-8-bromo-pyrazolo[1,5-a][1,3,5]triazine | H | 160–162 |
| 59 | phenyl | 3-OMe | 4-OMe | 5-OMe | 4-methyl-2-n-butyl-pyrazolo[1,5-a][1,3,5]triazine | 3,4,5-trimethoxybenzoyl | 93–95 |
| 60 | phenyl | 2-CF₃ | H | H | 4-methyl-2-n-butyl-pyrazolo[1,5-a][1,3,5]triazine | 2-(trifluoromethyl)benzoyl | 128–130 |
| 61 | phenyl | 2-Cl | H | H | 4-methyl-2-n-butyl-pyrazolo[1,5-a][1,3,5]triazine | 2-chlorobenzoyl | 90–92 |
| 62 | phenyl | 2-NO₂ | H | H | 4-methyl-2-n-butyl-pyrazolo[1,5-a][1,3,5]triazine | 2-nitrobenzoyl | 146–148 |

¹H-NMR data on the compound of Example 43 shown in Table 2 are presented below.
0.88 (3H, t, J=7.4), 1.2–1.4 (2H, m),
1.5–1.7 (2H, m), 2.47 (3H, s), 2.66 (2H, t, J=6.9), 6.55 (1H, d, J=2.0), 7.2–7.4 (2H, m),
7.43 (1H, t, J=7.4), 7.62 (1H, d, J=6.9),
8.21 (1H, d, J=2.0), 11.6–11.9 (1H, brs).

EXAMPLES 63–75

The compounds set forth in Table 3 were prepared in a similar manner as in Example 1. Table 3 shows the structures and melting points of the compounds obtained.

EXAMPLES 76–82

The compounds shown as Examples 76–82 in Table 3 were isolated from the former fractions of silica gel chromatography in Examples 63–64 and 68–72 respectively. Table 3 shows the structures and melting points of the compounds obtained.

EXAMPLE 83

Using the compound obtained in Example 75, the compound shown in Table 3 was prepared in a similar manner as in Example 56. Table 3 shows the structure and melting point of the compound obtained.

EXAMPLES 84–120

The following compounds can be prepared by subjecting suitable starting materials to similar reactions as in Reference Examples or Examples.

EXAMPLE 84
N-(2-n-butylthieno[3,2-d]pyrimidin-4-yl)-1-naphthoylamide

EXAMPLE 85
N-(2-n-butyl-9H-purin-6-yl)-1-naphthoylamide

EXAMPLE 86
N-(1-benzyl-6-n-butyl-1H-pyrazolo[3,4-d]pyrimidin-4-yl)-1-naphthoylamide EXAMPLE 87
N-(8-bromo-2-n-butylpyrazolo[1,5-a]-1,3,5-triazin-4-yl)-1-naphthoylamide EXAMPLE 88
N-(2-n-butylthieno[3,2-d]pyrimidin-4-yl)nicotinamide EXAMPLE 89
N-(2-n-butyl-9H-purin-6-yl)nicotinamide EXAMPLE 90
N-(1-benzyl-6-n-butyl-1H-pyrazolo[3,4-d]pyrimidin-4-yl)nicotinamide EXAMPLE 91
N-(8-bromo-2-n-butylpyrazolo[1,5-a]-1,3,5-triazin-4-yl)nicotinamide EXAMPLE 92
N-(2-n-butylthieno[3,2-d]pyrimidin-4-yl)-2-furancarboxyamide EXAMPLE 93
N-(2-n-butyl-9H-purin-6-yl)-2-furancarboxyamide EXAMPLE 94
N-(1-benzyl-6-n-butyl-1H-pyrazolo[3,4-d]pyrimidin-4-yl)-2-furancarboxyamide EXAMPLE 95
N-(8-bromo-2-n-butylpyrazolo[1,5-a]-1,3,5-triazin-4-yl)-2-furancarboxyamide EXAMPLE 96
N-(1-benzyl-6-n-butyl-1H-pyrazolo[3,4-d]pyrimidin-4-yl)-3-chlorobenzamide EXAMPLE 97
N-(2-benzyl-6-n-butyl-2H-pyrazolo[3,4-d]pyrimidin-4-yl)-3-chlorobenzamide EXAMPLE 98
N-(9-benzyl-2-n-butyl-9H-purin-6-yl)-3-chlorobenzamide EXAMPLE 99
N-(7-benzyl-2-n-butyl-7H-purin-6-yl)-3-chlorobenzamide EXAMPLE 100
N-(1-benzyl-6-n-butyl-1H-pyrazolo[3,4-d]pyrimidin-4-yl)-2-methoxybenzamide EXAMPLE 101
N-(2-benzyl-6-n-butyl-2H-pyrazolo[3,4-d]pyrimidin-4-yl)-2-methoxybenzamide EXAMPLE 102
N-(9-benzyl-2-n-butyl-9H-purin-6-yl)-2-methoxybenzamide EXAMPLE 103
N-(7-benzyl-2-n-butyl-7H-purin-6-yl)-2-methoxybenzamide EXAMPLE 104
N-(2-n-butyl-7-phenylpyrazolo[1,5-a]-1,3,5-triazin-4-yl)-3-chlorobenzamide EXAMPLE 105
N-(2-n-butyl-7-phenylpyrazolo[1,5-a]-1,3,5-triazin-4-yl)-2-methoxybenzamide EXAMPLE 106
N-(2-n-butyl-8-phenylpyrazolo[1,5-a]-1,3,5-triazin-4-yl)-3-chlorobenzamide EXAMPLE 107
N-(2-n-butyl-8-phenylpyrazolo[1,5-a]-1,3,5-triazin-4-yl)-2-methoxybenzamide EXAMPLE 108
N-[2-n-butyl-8-(4-phenylthiophenyl)pyrazolo[1,5-a]-1,3,5-triazin-4-yl]-3-chlorobenzamide EXAMPLE 109
N-[2-n-butyl-8-(4-phenylthiophenyl)pyrazolo[1,5-a]-1,3,5-triazin-4-yl]-2-methoxybenzamide EXAMPLE 110
N-(9-benzyl-2-n-butyl-9H-purin-6-yl)-1-naphthoylamide EXAMPLE 111
N-(9-benzyl-2-n-butyl-9H-purin-6-yl)nicotinamide EXAMPLE 112
N-(9-benzyl-2-n-butyl-9H-purin-6-yl)-2-furancarboxyamide EXAMPLE 113
N-(7-benzyl-2-n-butyl-7H-purin-6-yl)-1-naphthoylamide EXAMPLE 114
N-(7-benzyl-2-n-butyl-7H-purin-6-yl)nicotinamide EXAMPLE 115
N-(7-benzyl-2-n-butyl-7H-purin-6-yl)-2-furancarboxyamide EXAMPLE 116
N-(2-benzyl-6-n-butyl-2H-pyrazolo[3,4-d]pyrimidin-4-yl)-1-naphthoylamide EXAMPLE 117
N-(2-benzyl-6-n-butyl-2H-pyrazolo[3,4-d]pyrimidin-4-yl)nicotinamide EXAMPLE 118
N-(2-benzyl-6-n-butyl-2H-pyrazolo[3,4-d]pyrimidin-4-yl)-2-furancarboxyamide EXAMPLE 119
N-(8-bromo-2-n-butylpyrazolo[1,5-a]-1,3,5-triazin-4-yl)-3-chlorobenzamide EXAMPLE 120
N-(8-bromo-2-n-butylpyrazolo[1,5-a]-1,3,5-triazin-4-yl)-2-methoxybenzamide

TABLE 3

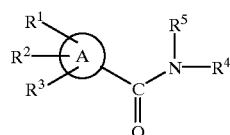

Me = Methyl group, Et = Ethyl group, n-Pr = n-Propyl group, n-Bu = n-Butyl group,
t-Bu = t-Butyl group, n-Pe = n-Pentyl group, Ac = Acetyl group, Ph = Phenyl group

| Example | A— | R¹ | R² | R³ | R⁴ | R⁵ | Melting point (° C.) |
|---|---|---|---|---|---|---|---|
| 63 | phenyl | H | H | H | 4-methyl-2-(n-Bu)-thieno[3,2-d]pyrimidinyl | H | 97–99 |
| 64 | phenyl | 2-Cl | H | H | 4-methyl-2-(n-Bu)-thieno[3,2-d]pyrimidinyl | H | 99–101 |
| 65 | phenyl | 2-OMe | H | H | 4-methyl-2-(n-Bu)-thieno[3,2-d]pyrimidinyl | H | 122–124 |
| 66 | phenyl | 3-OMe | 4-OMe | 5-OMe | 4-methyl-2-(n-Pr)-thieno[3,2-d]pyrimidinyl | H | 86–88 |
| 67 | phenyl | 2-Cl | 4-Cl | H | 4-methyl-2-(n-Bu)-thieno[3,2-d]pyrimidinyl | H | 139–141 |
| 68 | phenyl | 3-Cl | H | 5-OMe | 4-methyl-2-(n-Bu)-thieno[3,2-d]pyrimidinyl | H | 74–76 |
| 69 | phenyl | 4-Cl | H | H | 4-methyl-2-(n-Bu)-thieno[3,2-d]pyrimidinyl | H | 129–131 |

TABLE 3-continued

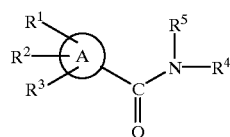

Me = Methyl group, Et = Ethyl group, n-Pr = n-Propyl group, n-Bu = n-Butyl group,
t-Bu = t-Butyl group, n-Pe = n-Pentyl group, Ac = Acetyl group, Ph = Phenyl group

| Example | A— | R¹ | R² | R³ | R⁴ | R⁵ | Melting point (° C.) |
|---|---|---|---|---|---|---|---|
| 70 | phenyl | 3-OMe | H | H | 4-methyl-2-n-butyl-thieno[3,2-d]pyrimidinyl | H | 117–119 |
| 71 | phenyl | 4-OMe | H | H | 4-methyl-2-n-butyl-thieno[3,2-d]pyrimidinyl | H | 100–102 |
| 72 | phenyl | 2-CF₃ | H | H | 4-methyl-2-n-butyl-thieno[3,2-d]pyrimidinyl | H | 155–157 |
| 73 | phenyl | 2-OMe | 3-OMe | 4-OMe | 4-methyl-2-n-butyl-thieno[3,2-d]pyrimidinyl | H | 100–102 |
| 74 | phenyl | 2-SMe | H | H | 4-methyl-2-n-butyl-thieno[3,2-d]pyrimidinyl | H | 123–125 |
| 75 | phenyl | 2-OAc | 3-OMe | H | 4-methyl-2-n-butyl-pyrazolo[1,5-a][1,3,5]triazinyl | H | 114–117 |
| 76 | phenyl | H | H | H | 4-methyl-2-n-butyl-thieno[3,2-d]pyrimidinyl | benzoyl | 155–157 |

TABLE 3-continued
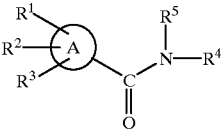
Me = Methyl group, Et = Ethyl group, n-Pr = n-Propyl group, n-Bu = n-Butyl group,
t-Bu = t-Butyl group, n-Pe = n-Pentyl group, Ac = Acetyl group, Ph = Phenyl group
| Example | A— | $R^1$ | $R^2$ | $R^3$ | $R^4$ | $R^5$ | Melting point (° C.) |
|---|---|---|---|---|---|---|---|
| 77 | 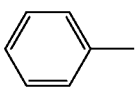 | 2-Cl | H | H | 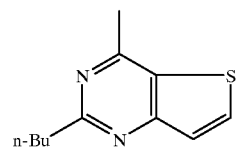 | 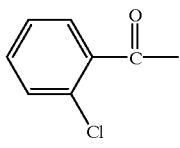 | 111–113 |
| 78 | 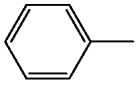 | 3-Cl | H | H | 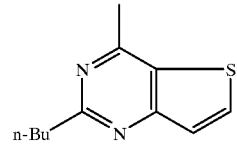 | 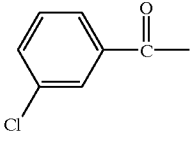 | 142–144 |
| 79 | 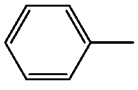 | 4-Cl | H | H | 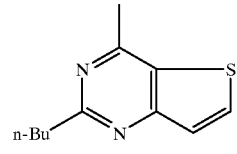 | 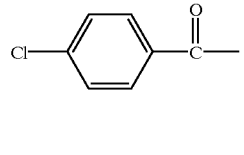 | 186–188 |
| 80 | 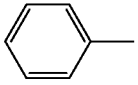 | 3-OMe | H | H | 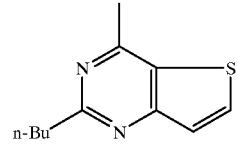 | 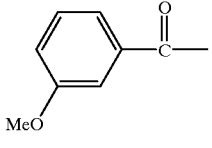 | 134–136 |
| 81 | 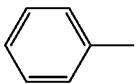 | 4-OMe | H | H | 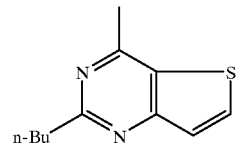 | 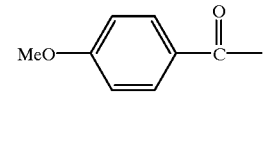 | 140–142 |
| 82 | 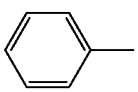 | 2-CF$_3$ | H | H | 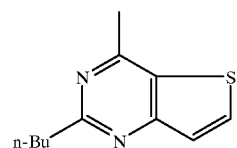 | 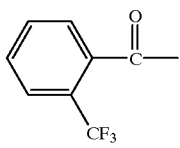 | 133–135 |
| 83 | 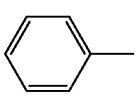 | 2-OH | 3-OMe | H | 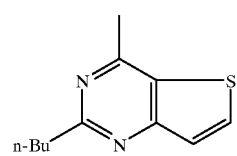 | H | 163–165 |

Pharmacological Test Example 1

Using 6-week-old male S.D. rats (n=7/group), the pain threshold of each rat's left hind paw was determined using Analgesy-Meter (product of Unicom) in accordance with the Randall-Sellitto method [Randall, L. O. and Sellitto, J. J., Arch. Int. Pharmacodyn., 111, 409 (1957)]. The value thus obtained was termed "pre-value".

One hour after measurement of the pre-value, a 5% gum arabic suspension containing the active ingredient compound of the invention was orally administered to the rats of the test group in an amount of 10 ml/kg so that the dosage of the active ingredient compound of the invention was 10 mg/kg, whereas a 5% gum arabic suspension (not containing the active ingredient compound of the invention) was orally administered to the rats of the control group in an amount of 10 ml/kg. One hour later, an aqueous physiological saline solution containing substance P (25 ng/0.1 ml) was subcutaneously injected into the left hind paw of each rat.

The pain threshold of each rat's left hind paw was determined in the same manner as above at a predetermined interval from the time of the substance P injection. The value thus obtained was termed "post-value".

The recovery (%) of the pain threshold was calculated from post-values and pre-values of the rats in each group, by means of the following formula.

$$\text{Recovery of pain threshold (\%)} = \frac{(\text{Test group average post-value}) - (\text{Control group average post-value})}{(\text{Control group average pre-value}) - (\text{Control group average post-value})} \times 100$$

The results (the highest recovery %) are shown in Table 4.

TABLE 4

| Example No. | Recovery (%) | Time from substance P injection (minutes later) |
|---|---|---|
| 1 | 69.2 | 60 |
| 7 | 39.3 | 15 |
| 14 | 54.1 | 60 |
| 15 | 83.2 | 30 |
| 16 | 47.9 | 30 |
| 17 | 74.7 | 60 |
| 21 | 34.4 | 60 |
| 33 | 57.7 | 60 |
| 34 | 41.8 | 30 |
| 44 | 56.8 | 60 |
| 47 | 50.0 | 30 |
| 48 | 68.5 | 30 |
| 59* | 30.5 | 60 |
| 61 | 35.9 | 60 |
| 64 | 63.7 | 30 |
| 66 | 31.3 | 30 |
| 70 | 30.4 | 30 |

*: administration amount = 1 mg/kg

Table 4 clearly shows that the compounds of the invention have high analgesic activity.

Formulation Example 1
Manufacture of Tablets

Tablets (1000 tables) for oral administration, each containing as an active ingredient 5 mg of the compound obtained in Example 1, were manufactured according to the following formula:

| | |
|---|---|
| Compound of the invention obtained in Example 1 | 5 g |
| Lactose (Japanese pharmacopoeia: JP) | 50 g |
| Corn starch (JP) | 25 g |
| Crystalline cellulose (JP) | 25 g |
| Methyl cellulose (JP) | 1.5 g |
| Magnesium stearate (JP) | 1 g |

More specifically, the compound of the invention obtained in Example 1, lactose, corn starch and calcium carboxymethyl cellulose were fully blended and granulated using an aqueous methyl cellulose solution. The granulated mixture was passed through a 24-mesh sieve, and the granules under the sieve were mixed with magnesium stearate and compression-molded into the objective tablets.

Formulation Example 2
Manufacture of Capsules

Two-piece hard gelatin capsules (1000 units) for oral administration, each containing as an active ingredient 10 mg of the compound obtained in Example 7, were manufactured according to the following formula:

| | |
|---|---|
| Compound of the invention obtained in Example 7 | 10 g |
| Lactose (JP) | 80 g |
| Corn starch (JP) | 30 g |
| Talc (JP) | 5 g |
| Magnesium stearate (JP) | 1 g |

More specifically, the above ingredients were finely pulverized and blended to give a homogeneous composition. This composition was filled into proper-sized capsule shells for oral administration to provide the objective encapsulated composition.

INDUSTRIAL APPLICABILITY

The amide derivatives of the present invention have highly potent analgesic effects and are useful as analgesics in the field of medicine.

What is claimed is:

1. An amide compound represented by the formula,

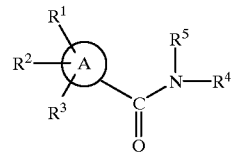

wherein ring A represents a benzene ring or a naphthalene ring; when ring A is a naphthalene ring, $R^1$, $R^2$ and $R^3$ are all hydrogen atoms, and when ring A is a benzene ring, $R^1$, $R^2$ and $R^3$ are the same or different and independently represent hydrogen, lower alkoxy, halogen, nitro, lower alkyl, halogen-substituted lower alkyl, phenyl, phenoxy, lower alkanoyloxy, hydroxy, lower alkylthio, lower alkyl sulfinyl or lower alkyl sulfonyl;

$R^4$ represents a heterocyclic group selected from the group consisting of (1) a lower alkyl-substituted thieno[3,2-d]-pyrimidin-4-yl group, (2) a pyrazolo [1,5-a]-1,3,5-triazin-4-yl group optionally having one or two substituents selected from the group consisting of lower alkyl, phenyl, phenyl(lower)alkyl, phenylthiophenyl and halogen, (3) a pyrazolo[3,4-d]pyrimidin-4-yl group which has a lower alkyl group at the 6-position and one of those nitrogen atoms may have a phenyl(lower) alkyl group as a substituent, and (4) a purin-6-yl group which has a lower alkyl group at the 2-position and one of whose nitrogen atoms may have a lower alkyl or phenyl (lower) group as a substituent; and $R^5$ represents a hydrogen atom or a group represented by

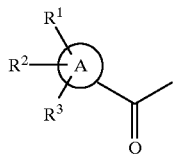

wherein A, $R^1$, $R^2$ and $R^3$ are as defined above.

2. An amide compound according to claim 1 which is represented by the formula of claim 1 wherein ring A represents a benzene ring.

3. An amide compound according to claim 2 which is represented by the formula of claim 1 wherein $R^4$ represents a thieno[3,2-d]pyrimidin-4-yl group substituted by a lower alkyl group at the 2-position, or a pyrazolo[1,5-a]-1,3,5-triazin-4-yl group substituted by a lower alkyl group at the 2-position.

4. An amide compound according to claim 3 which is represented by the formula of claim 1 wherein $R^1$, $R^2$ and $R^3$ are the same or different and independently represent hydrogen, lower alkoxy, halogen, phenyl, lower alkanoyloxy or lower alkylthio.

5. An amide compound according to claim 4 which is selected from the group consisting of N-(2-n-butylpyrazolo[1,5-a]-1,3,5-triazin-4-yl)-3,4,5-trimethoxy benzamide, N-(2-n-butylpyrazolo[1,5-a]-1,3,5-triazin-4-yl)-2,4-dichlorobenzamide, N-(2-n-butylpyrazolo[1,5-a]-1,3,5-triazin-4-yl)-3-chlorobenzamide and N-(2-n-butylthieno[3,2-d]pyrimidin-4-yl)-3,4,5-trimethoxybenzamide.

6. An analgesic composition which comprises an amide compound defined in claim 1 and a pharmaceutically acceptable carrier.

7. A method for relieving pain, which comprises administering to a patient an effective amount of an amide compound defined in claim 1.

* * * * *